US011000741B2

(12) United States Patent
Khan et al.

(10) Patent No.: US 11,000,741 B2
(45) Date of Patent: May 11, 2021

(54) MULTIPLE MEMORY MATERIALS AND SYSTEMS, METHODS AND APPLICATIONS THEREFOR

(71) Applicant: SMARTER ALLOYS INC., Waterloo (CA)

(72) Inventors: Mohammad Ibrahem Khan, Waterloo (CA); Andrew Nikolas Pequegnat, Waterloo (CA)

(*) Notice: Subject to any disclaimer, the term of this patent is extended or adjusted under 35 U.S.C. 154(b) by 416 days.

(21) Appl. No.: 15/325,901

(22) PCT Filed: Jul. 14, 2015

(86) PCT No.: PCT/CA2015/050654
§ 371 (c)(1),
(2) Date: Jan. 12, 2017

(87) PCT Pub. No.: WO2016/008043
PCT Pub. Date: Jan. 21, 2016

(65) Prior Publication Data
US 2017/0165532 A1    Jun. 15, 2017

Related U.S. Application Data

(60) Provisional application No. 62/023,995, filed on Jul. 14, 2014, provisional application No. 62/055,775, filed on Sep. 26, 2014.

(51) Int. Cl.
*A63B 53/04* (2015.01)
*A61C 7/20* (2006.01)
(Continued)

(52) U.S. Cl.
CPC ............ *A63B 53/04* (2013.01); *A61C 5/42* (2017.02); *A61C 7/20* (2013.01); *A61F 2/82* (2013.01);
(Continued)

(58) Field of Classification Search
CPC .. A63B 53/04; A61C 5/42; A61C 7/20; A61F 2/82; A61L 31/14; A61L 31/022
(Continued)

(56) References Cited

U.S. PATENT DOCUMENTS

| 4,895,438 A | 1/1990 | Zider et al. |
| 5,437,282 A | 8/1995 | Koger et al. |

(Continued)

FOREIGN PATENT DOCUMENTS

| CA | 2770122 | 2/2011 |
| CN | 102665891 A | 9/2012 |
| WO | WO 02/26410 | 4/2002 |

OTHER PUBLICATIONS

Canadian Intellectual Property Office as International Receiving Office, Search Report and Written Opinion on PCT Appln. No. PCT/CA2015/050654, dated Oct. 19, 2015.
(Continued)

*Primary Examiner* — Collin X Beatty
*Assistant Examiner* — Grant A Gagnon
(74) *Attorney, Agent, or Firm* — Gowling WLG (Canada) LLP; Neil W. Henderson

(57) ABSTRACT

An apparatus for fabrication of a multiple memory material including: a feeding assembly for feeding shape memory material; a processing station aligned with the feeding assembly to receive the shape memory material to be processed; at least one energy source aligned with an energy source aperture to provide energy to the shape memory material; a shielding gas provider attached to a shielding gas engagement portion to provide shielding gas; and a controller configured to control the feeding assembly, the shielding gas provider and the energy source according to predetermined parameters to form the multiple memory material. A method for fabricating a multiple memory material includ-
(Continued)

ing: determining process parameters for the shape memory material, via a controller; receiving shape memory material at a feeding assembly; feeding the shape memory material, via the feed assembly, to a processing station; providing shielding gas to the processing station, via a shielding gas provider; and providing energy to the shape memory material, via at least one energy source, based on the process parameters to produce the multiple memory material.

20 Claims, 19 Drawing Sheets

(51) Int. Cl.
*A61F 2/82* (2013.01)
*A61C 5/42* (2017.01)
*G02C 5/16* (2006.01)
*A61L 31/02* (2006.01)
*A61L 31/14* (2006.01)
*B22F 3/24* (2006.01)
*B23K 26/08* (2014.01)
*B22F 3/105* (2006.01)
*B33Y 40/00* (2020.01)
*C22F 1/00* (2006.01)
*B33Y 10/00* (2015.01)
*B32B 15/00* (2006.01)
*B33Y 30/00* (2015.01)
*B23K 26/14* (2014.01)
*B23K 26/12* (2014.01)
*B23K 26/0622* (2014.01)
*B32B 15/14* (2006.01)
*B32B 27/40* (2006.01)
*B32B 27/36* (2006.01)
*B32B 27/12* (2006.01)
*B23K 26/354* (2014.01)
*B23K 26/00* (2014.01)
*G02C 5/00* (2006.01)
*G02C 5/14* (2006.01)
*B23K 103/14* (2006.01)
*B29C 71/04* (2006.01)

(52) U.S. Cl.
CPC ............. *A61L 31/022* (2013.01); *A61L 31/14* (2013.01); *B22F 3/1055* (2013.01); *B22F 3/24* (2013.01); *B23K 26/0006* (2013.01); *B23K 26/0622* (2015.10); *B23K 26/08* (2013.01); *B23K 26/0823* (2013.01); *B23K 26/12* (2013.01); *B23K 26/123* (2013.01); *B23K 26/14* (2013.01); *B23K 26/354* (2015.10); *B32B 15/00* (2013.01); *B32B 15/14* (2013.01); *B32B 27/12* (2013.01); *B32B 27/36* (2013.01); *B32B 27/40* (2013.01); *B33Y 10/00* (2014.12); *B33Y 30/00* (2014.12); *B33Y 40/00* (2014.12); *C22F 1/006* (2013.01); *G02C 5/008* (2013.01); *G02C 5/143* (2013.01); *G02C 5/16* (2013.01); *A61C 2201/007* (2013.01); *A61F 2210/0014* (2013.01); *A61L 2400/16* (2013.01); *A63B 2209/00* (2013.01); *B22F 2003/1056* (2013.01); *B22F 2998/00* (2013.01); *B23K 2103/14* (2018.08); *B29C 71/04* (2013.01); *B29C 2791/009* (2013.01); *B32B 2250/02* (2013.01); *B32B 2307/20* (2013.01); *B32B 2307/51* (2013.01); *B32B 2307/714* (2013.01); *B32B 2437/00* (2013.01); *B32B 2535/00* (2013.01); *Y02P 10/295* (2015.11)

(58) Field of Classification Search
USPC .......................................................... 351/114
See application file for complete search history.

(56) References Cited

U.S. PATENT DOCUMENTS

| 5,683,245 | A | 11/1997 | Sachdeva et al. |
| 5,899,818 | A | 5/1999 | Zider et al. |
| 6,669,794 | B1 | 12/2003 | Bellouard et al. |
| 8,074,431 | B1 * | 12/2011 | Pierson ................ B65G 47/086 414/791.6 |
| 2007/0042660 | A1 | 2/2007 | Waxler |
| 2007/0054238 | A1 | 3/2007 | Hof et al. |

OTHER PUBLICATIONS

Andrew Pequegnat: "Novel Laser Based NiTi Shape Memory Alloy Processing Protocol for Medical Device Applications, Chapter 3", Apr. 1, 2014, pp. 42-53, XP055444510.
Extended European Search Report on corresponding EP patent application No. 15821859.4, dated Jun. 1, 2018.
Office Action on corresponding CN patent application No. 201580043733.6, dated May 9, 2019.
English translation of Abstract of CN102665891A, retrieved from Espacenet Jun. 25, 2019.

* cited by examiner

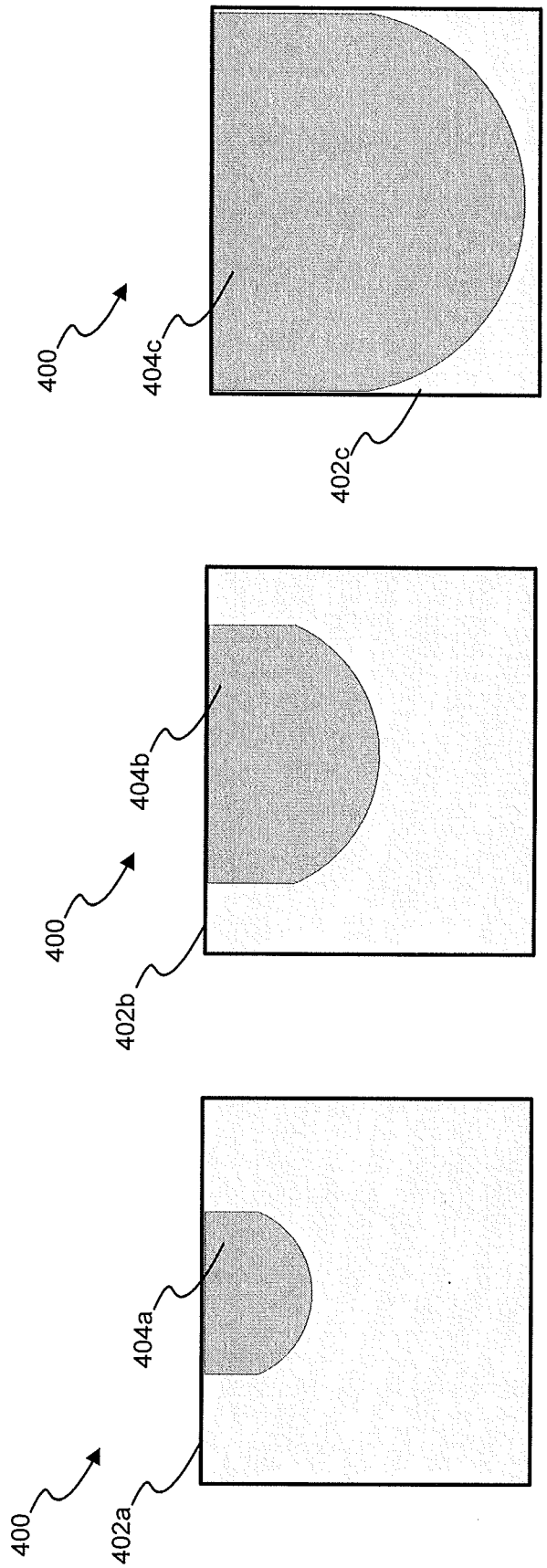

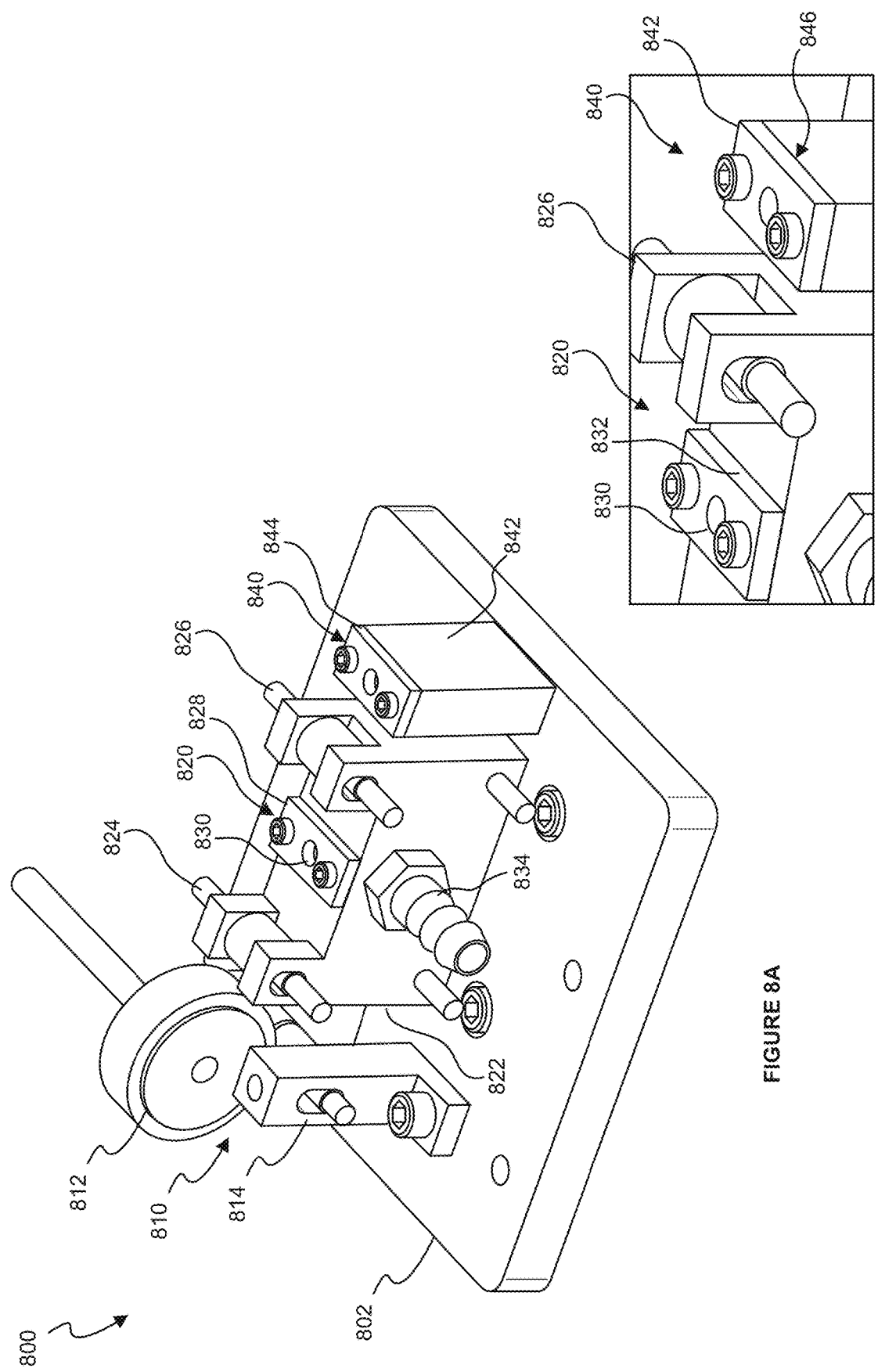

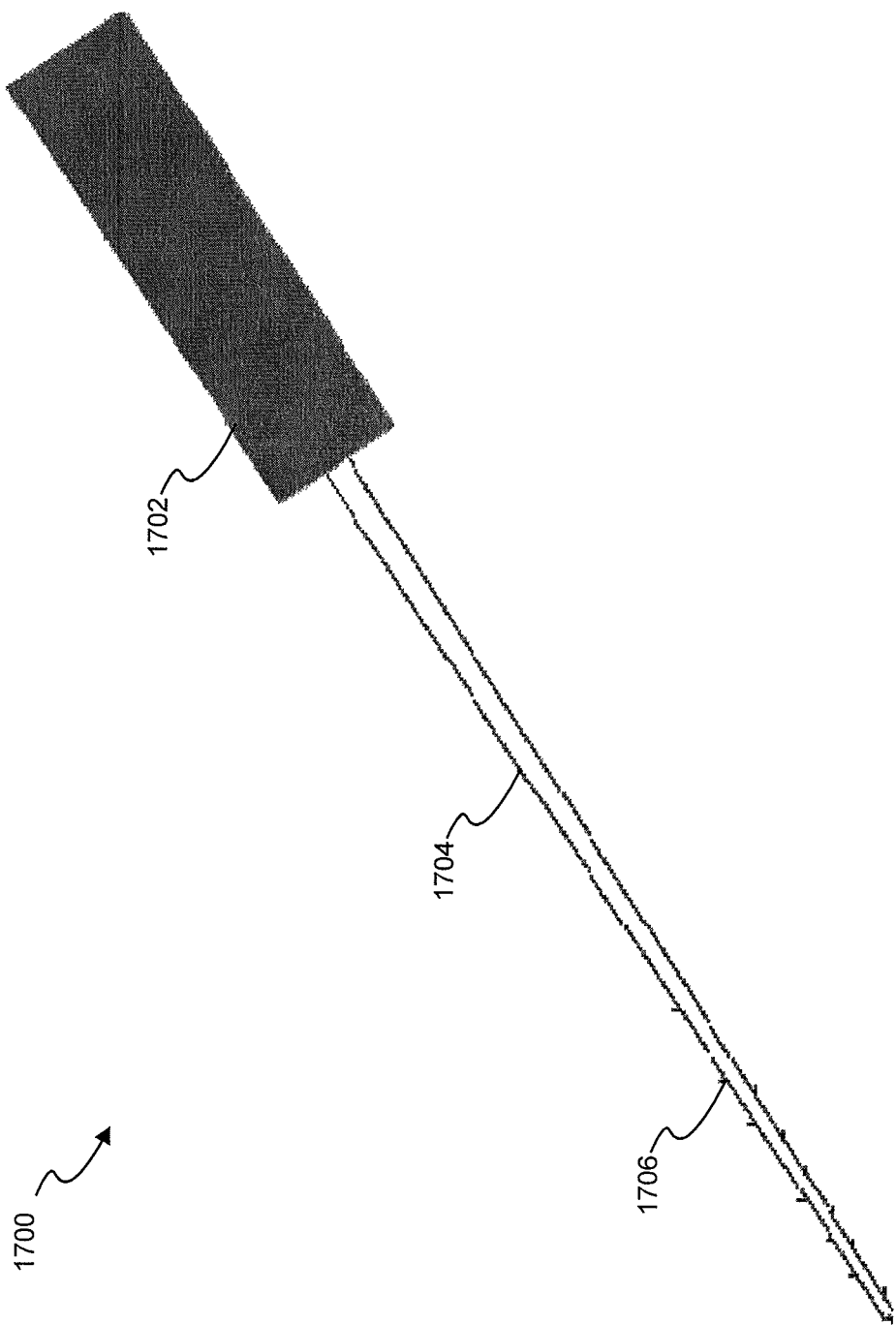

MULTIPLE MEMORY MATERIALS AND SYSTEMS, METHODS AND APPLICATIONS THEREFOR

RELATED APPLICATIONS

The present application claims priority from U.S. Provisional Patent Application No. 62/023,995 filed Jul. 14, 2014 and from U.S. Provisional Patent Application No. 62/055,775 filed Sep. 26, 2014 both of which are incorporated herein by reference.

FIELD

The present disclosure relates generally to multiple memory materials and the processing of shape memory materials. More particularly, the present disclosure relates to methods and systems for processing or treating shape memory materials to create multiple memory materials.

BACKGROUND

Generally speaking, shape memory materials are materials that are malleable at a lower temperature and can be trained to hold and return to a particular shape when at a higher temperature. Even if bent into a different shape when at the lower temperature, the material returns to the trained shape when the temperature is raised. The temperature at which the material reverts to the trained high temperature configuration is typically referred to as the transformation temperature. The shape memory effect that occurs in these materials is related to a reversible solid state phase transition in which the material transforms between an austenitic state and a martensitic state with a change in temperature. In the martensitic state, the shape memory material becomes more easily deformed and is typically able to accommodate significant plastic deformation at an almost constant stress level. When the shape memory material is in the martensitic state and is heated and the metal returns to the austenitic state. The transformation may occur at a particular temperature or over a range of temperature.

Shape memory materials can be generally divided into shape memory metals/alloys (SMAs) and shape memory polymers (SMPs). Many alloys may be manipulated into a shape memory material, including some magnetic materials and alloys. Three main types of SMAs include:
1) Nickel-titanium (NiTi)
2) Copper-Zinc-Aluminum-Nickel
3) Copper-Aluminum-Nickel Other SMAs include, but are not limited to, the following:
1) Ag—Cd 44/49 at. % Cd
2) Au—Cd 46.5/50 at. % Cd
3) Cu—Al—Ni 14/14.5 wt. % Al and 3/4.5 wt. % Ni
4) Cu—Sn approx. 15 at. % Sn
5) Cu—Zn 38.5/41.5 wt. % Zn
6) Cu—Zn—X (X=Si, Al, Sn)
7) Fe—Pt approx. 25 at. % Pt
8) Mn—Cu 5/35 at. % Cu
9) Fe—Mn—Si
10) Pt alloys
11) Co—Ni—Al
12) Co—Ni—Ga
13) Ni—Fe—Ga
14) Ti—Pd in various concentrations
15) Ni—Ti (~55% Ni)
(at. %=atomic percent)

Examples of SMPs include, but are not limited to, the following:
1) Polyurethane-based shape-memory polymers with ionic or mesogenic components
2) Polyethylene-terephthalate-Polyethyleneoxide (PET-PEO) block copolymer crosslinked using Maleic Anhydride One of the most common shape memory materials is nitinol (sometimes referred to as NiTi), an alloy of nickel and titanium. This application focuses on SMAs and nitinol in particular, however, similar principles can apply to other SMAs, SMPs or shape memory materials, as will be understood by one skilled in the art upon reading the present document.

An application of shape memory materials is to exploit the force profile of the material when the shape memory material is heated and the shape memory material transitions from the martensitic state to the austenitic state. However, conventional shape memory materials are limited to the extent and preciseness at which these forces may be fabricated and tailored.

In order to process shape memory materials, conventional processing methods and systems require near constant manual manipulation by an operator. These processing techniques can be typically slow and inefficient. As well, conventional processing methods and systems may require processing under a sealed workstation when working with a shielding gas for the safety of the operator. Without a shielding gas, there is a risk of having unwanted levels of impurities, for example high levels of oxygen, present in the treated material.

Based on the foregoing, there is a need for improved methods and systems for processing or treating shape memory materials in order to overcome or alleviate at least one of the concerns described above.

SUMMARY

In a first aspect, there is provided an apparatus for fabrication of a multiple memory material including: a feeding assembly for feeding shape memory material; a processing station aligned with the feeding assembly to receive the shape memory material to be processed, the processing station including: a material passageway passing though the processing station and aligned with the feeding assembly to receive and retain the shape memory material from the feeding assembly; and at least one energy source aperture aligned with the material passageway; a shielding gas engagement portion to provide shielding gas to the material passageway; at least one energy source aligned with the energy source aperture to provide energy to the shape memory material; a shielding gas provider attached to the shielding gas engagement portion to provide shielding gas; and a controller configured to control the feeding assembly, the shielding gas provider and the energy source according to predetermined parameters to form the multiple memory material.

In a particular case, the shielding gas engagement portion may be located on a lateral side of the processing station and the at least one energy source aperture may be located on a top portion of the processing station.

In another particular case, the processing station further may include a first and a second roller assembly for retaining the material.

In still another particular case, the feeding assembly may include an upper roller assembly and a lower roller assembly wherein one of the roller assemblies is driven by a motor and the other roller assembly is free spinning.

In yet another particular case, the feeding assembly may be a robotic arm.

In still yet another particular case, the feeding assembly may feed the material to the processing station in a continuous feed.

In another particular case, the feeding assembly may feed the material to the processing station in a stepped manner.

In still another particular case, the apparatus may further include a guidance assembly proximate to the processing station configured to guide the multiple memory material after exiting the processing station.

In yet another particular case, the multiple memory material may be a wire and the material passageway is configured to generally match the size of the wire while still allowing movement of the wire through the material passageway.

In still yet another particular case, the multiple memory material may be a sheet and the material passageway is configured to generally match the size of the sheet while still allowing movement of the sheet through the material passageway.

In another aspect, there is provided a method for fabricating a multiple memory material including: determining process parameters for the shape memory material, via a controller; receiving shape memory material at a feeding assembly; feeding the shape memory material, via the feed assembly, to a processing station; providing shielding gas to the processing station, via a shielding gas provider; and providing energy to the shape memory material, via at least one energy source, based on the process parameters to produce the multiple memory material.

In a particular case, the method may further include: determining if there are additional areas of the shape memory material to process; and feeding the shape memory material through the processing station to the additional area for processing.

In another particular case, the multiple memory material may be a wire.

In still another particular case, the multiple memory material may be a sheet.

In yet another aspect, there is provided a medical stent including a region of greater elasticity and a region of lesser elasticity, wherein the stent is fabricated according to the method for fabricating multiple memory material.

In still another aspect, there is provided a pair of eyeglasses having: a frame; two multiple memory arms extending from the frame, wherein each arm includes: a first portion at a proximate end of the arm composed of unprocessed shape memory material; and a second portion at a lateral end of the arm composed of shape memory material, processed according the method for fabricating multiple memory material, wherein the second portion is substantially in-line with the first portion at a first temperature and wherein the second portion is adapted to change profile when heated to a second temperature.

In a further aspect, there is provided a textile including a multiple memory material processed according to the method for fabricating multiple memory material, wherein the material is covered by the textile and is configured to adjust the shape of the textile based on changes in temperature.

In still another aspect, there is provided a golf club head including: a body; and a face mounted to the front of the body, wherein the face comprises a multiple memory material processed according to the method for fabricating multiple memory material to have different pseudo-elastic properties in different areas of the face.

In yet another aspect, there is provided an endodontic file comprising: a handle; and a filing wand connected to the handle, the filing wand including a multiple memory wire provided with multiple pseudo-elastic properties to adapt to the shape of a root canal.

In still another aspect, there is provided an orthodontic archwire comprising a plurality of force regions having differing tensile force, wherein the archwire is fabricated according to the method for fabricating multiple memory material.

Other aspects and features of the present disclosure will become apparent to those ordinarily skilled in the art upon review of the following description of specific embodiments in conjunction with the accompanying figures.

BRIEF DESCRIPTION OF FIGURES

Embodiments of the present disclosure will now be described, by way of example only, with reference to the attached Figures.

FIGS. 4A, 4B and 4C illustrate a cross-sectional view of an example shape memory material having energy applied;

FIGS. 8A to 8F illustrate an apparatus for fabrication of a MMM, according to another embodiment;

FIG. 13 illustrates a side view of an endodontic file using MMM;

DETAILED DESCRIPTION

Figure 1:
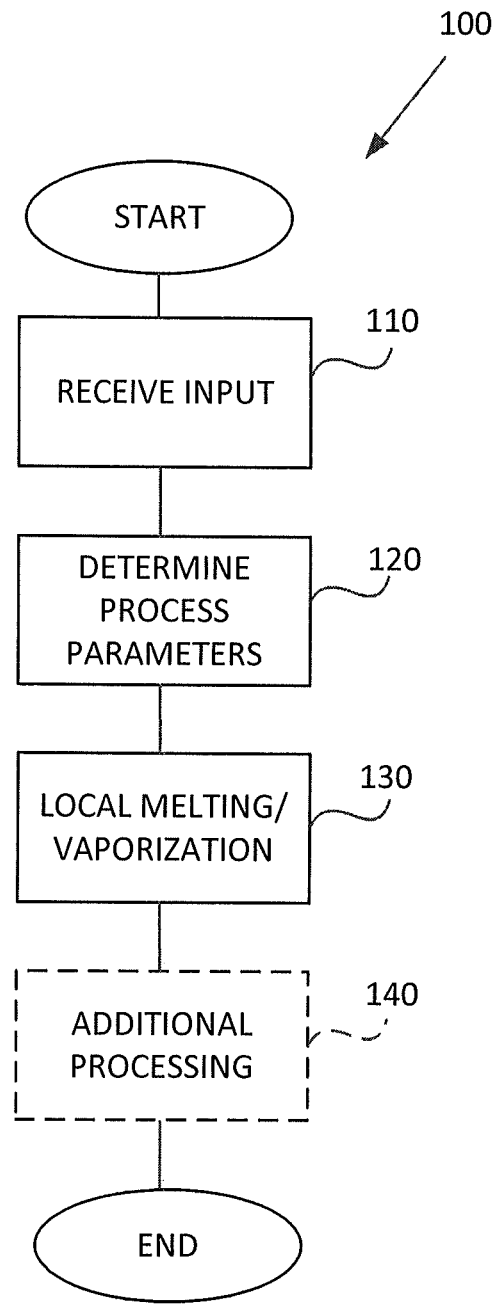
FIG. 1 is a flow chart of an example method of treating/forming a piece of nitinol into a multiple memory material (MMM) having multiple transformation temperatures.

Generally, the present disclosure provides methods, apparatuses and systems for processing materials to create multiple memory materials and applications thereof.

While the discussion below focuses on shape memory alloys (SMAs), it will be understood that the principles, processes and systems can be similarly applied to other shape memory materials; for example, shape memory metals and shape memory polymers. Multiple memory materials are described in further detail in Patent Cooperation Treaty Application No. PCT/CA2010/001219, filed Aug. 6, 2010, which is hereby incorporated herein by reference. Further, while the discussion below focuses on a laser as an energy source, the energy source may include other devices/materials for applying energy, for example, electron beams, electrical arcs, ion beams or the like.

Traditional shape memory materials are batch processed to produce a monolithic sheet having a single transformation temperature. This processing is most appropriate due to the homogeneous composition and structure within the shape memory material. Thus, this processing only allows the shape memory material to have a single transformation temperature for a given "remembered" shape.

The applicants have ascertained that during the local application of a laser on an area of a shape memory material (in this example, nitinol) local temperatures and partial pressure effects cause the melting and, it is believed, boiling of the material or constituents thereof. Testing indicates that the portion of the nitinol workpiece that was subject to the laser treatment exhibited a change in the transformation temperature for that portion/area that was treated. It appears that the melting of the nitinol and subsequent solidification causes a change in the local chemistry of the nitinol. Consequently the processed area exhibits an additional memory while the remaining untreated material still exhibited its original properties and memory. Thus, one or more additional memories may be embedded into a shape memory material such that the shape memory material may be a multiple memory material (MMM) having multiple transformation temperatures. As will be understood, having additional memories may enable additional functionality for many applications.

It is believed that the change in the transformation temperature is because the transformation temperature is very sensitive to the local structure and chemistry of the nitinol. Because of vaporization during melting (due to temperature and the partial pressures involved), the prior microstructure is destabilized until the point where the molten metal subsequently re-solidifies. In particular, in the case of nitinol, the original base material for NiTi is typically a homogeneous structure, which is saturated with either Nickel (when Ni is greater than 50 at. % (atomic percent)) or Titanium (when Ti is greater than 50 at. %). This structure is usually attained by annealing the alloy (between 500 and 1200 degrees Celsius) then quenching to retain the NiTi structure. In a particular case, annealing the alloy may be accomplished at approximately 800 degrees Celsius. Further, mechanical processing, such as rolling, may be conducted to refine the microstructure and add strength. However, when the structure is melted and re-solidified (for example, using a laser as described further below) one or more constituents may be vaporized while the remaining saturated constituents are pushed along with the solidification front with the final liquid to solidify being rich in that particular chemistry. This local area will then stabilize into an intermetallic (I.e. Ni rich: Ni3Ti Ni4Ti3; Ti Rich: Ti2Ni). This result may occur when there is an imbalance in composition and there may be other mechanisms involved as well. Although the overall chemistry of the re-solidified metal is generally the same (including matrix and intermetallic), the matrix chemistry will be different from the original base material. Hence, the matrix in the local area will have a different transformation temperature. Interestingly, in some cases, peak temperatures can remain high long enough that the local area also experiences some degree of post-processing heat treatment (such as annealing), which may include the heat affected zone.

The local melting of the shape memory material contrasts with some lower temperature forms of heat treatment of alloys/metals, such as annealing, because these lower temperature processes will have less impact on the internal structure and chemistry as they occur in the solid state rather than in a molten liquid state. Further, when conducted appropriately, the melting process does not result in the complete destruction of the super-elasticity of the shape memory material when in the martensitic state, although it may result in a change in the super-elasticity. Still further, the process can be performed on existing shape memory materials in contrast to processes that are used to form shape memory materials from base constituents.

FIG. 1 shows a flow chart of an example method 100 of treating/forming a monolithic sheet or workpiece of nitinol into a multiple memory material (MMM) having multiple transformation temperatures. It will be understood that this method may be adapted to process other shape memory materials to alter the local chemistry/structure to provide desired results, as described herein.

The method 100 starts with receiving a shape memory material as input 110, for example a monolithic sheet of nitinol. In some cases, the monolithic sheet or workpiece of nitinol may first be processed to impart a particular shape memory into the monolithic sheet 110. The processing of the nitinol to impart a first shape memory (and transformation temperature) is well known in the art. However, an unprocessed alloy having sufficient composition to exhibit the shape memory effect may also be processed using embodiments described herein. In this case a first memory can first be imparted using the method 100.

The nitinol workpiece is then moved to a processing station as input where it is positioned for treatment as follows.

At 120, process parameters are determined. For example, the method may include the use of a processor or the like to automatically calculate the process parameters to be used based on the desired transformation temperature, chemical composition or predetermined result of the processing. In other cases, the processor may retrieve predetermined process parameters previously stored in, for example, a memory component, database, or the like. An example of the types of information, including transformation temperatures as a function of NiTi chemistry and the like, that can be used in the calculation or in look-up tables or the like is of the type described in, for example, U.S. Patent Application Publication No. 2012/0192999 by Khan, or Tang W, Thermodynamic Study of the Low-Temperature Phase B19' and the Martensitic Transformation in Near-Equiatomic Ti—Ni Shape Memory Alloys, Metallurgical and Materials Transactions A, Volume 28A, March, 1997, pp. 537-544. It will be understood that this aspect of the embodiment may consist of computer readable instructions on a physical media that, when performed by or executed on a computing device (processor), cause the procedure to be performed.

The nitinol workpiece is then subjected to laser treatment 130 in an area that is intended to have the local chemistry altered, in this case, to provide a different transformation temperature. It will be understood that, depending on the application, a laser may be moved to ensure that the required area of the nitinol workpiece is laser treated, or alternatively, the nitinol workpiece may be moved in relation to the laser. In the laser treatment 130, energy is applied to a local area of the nitinol such that at least some local melting and vaporization occurs (based on the temperature and partial pressures at the local area). The range of melting points for shape memory materials such as nitinol is affected by the chemical makeup of the shape memory material as well as chemical changes that may occur in the heating process. The rate of vaporization is also affected by local pressure. For nitinol, some effect may be available after heating to a range of approximately 1,000 degrees Celsius and higher. This temperature range contrasts with some lower temperature forms of heat treatment of alloys/metals, such as annealing, because these processes will have less impact on the internal structure as they occur in the solid state rather than in a molten liquid state. In further particular cases, the nitinol may be heated to between approximately 1,250 and 1,280 degrees Celsius. In another case, the nitinol is heated to approximately 1,300 degrees Celsius or higher, for example in the range of approximately 1,320 or 1,340 degrees Celsius. Generally speaking, the temperature is selected in order to provide a sufficient level of melting and vaporization to occur such that the local chemistry is changed to provide the desired result, such as an additional transformation temperature.

The application of energy to generate the heating is preferably localized and configured so that the change in the local chemistry will be localized such that there is no or limited spread of the effect into other areas of the shape memory material sheet. In many cases, a shorter energy application process may provide a better defined area or zone of distinct change in local chemistry, and thus localized change in transformation temperature. As such, laser melting is preferred but other forms of heating such as resistance or plasma melting may also be used. In the case of laser melting, the appropriate temperature can typically be reached in as little as one millisecond or less in order to have very rapid heating and treatment of the shape memory material. In a particular case, the appropriate temperature may be reached in less than half a millisecond. With resistance or plasma heating the time of heat application can also be as little as one second or less.

Cooling and re-solidification of the treated material will occur quickly after the removal of the energy. Process parameters can be configured to provide controlled in-situ cooling rates. In-situ cooling control may be performed while the workpiece if being processed. For example, cooling and re-solidification can be controlled by using a heat sink for more rapid cooling (i.e. copper block as a chiller or a cold gas) or a heated stage for slower cooling rates.

In some cases, the nitinol workpiece may be subject to further processing 140, after initial processing has been completed, which may include further heat treatment as described in one example below or other processing, for example, cold working, heat treatments, surface finishing, cleaning, or the like, depending on a particular application for the multiple memory material.

In some cases, processing the shape memory material with the energy source includes processing with a laser. In one example, a neodymium-doped yttrium aluminum garnet (Nd:YAG) laser may be used. Several key parameters are used to control the pulsed Nd:YAG laser process. These parameters include but are not limited to: pulse width; peak power; frequency; laser movement speed (sometimes referred to as welding speed); and defocus distance. The pulse energy and average power are also used in order to conceptualize the amount of energy transferred to a material. An operator typically presets the peak power, pulse width and frequency on a laser machine. The peak power is the instantaneous power of the laser pulse and can influence the temperature rise of the material. Melting is initialized when there is sufficient heat to raise peak temperatures above the liquidus temperature of the workpiece. This process of raising peak temperature involves overcoming heat loss due to conduction and convection. The pulse width is the time each pulse irradiates the workpiece. The larger the pulse width the longer the time the peak power is applied. Finally, the pulse frequency is the number of times the laser is pulsed per second, which can be used to control the amount of pulse overlap and heat input to the workpiece. In this embodiment, a pulsed laser is used but this is not necessarily a requirement herein.

Laser movement speed and defocus distance are parameters that can also have an impact on the overall processing of a workpiece. The laser movement speed influences the amount of overlap on each spot size for a given pulse frequency. However the pulse frequency and laser movement speed are typically correlated to attain the desired spot overlap. In the field of welding, spot overlap is typically varied from about 50%, for strength of weld applications, and 80% for applications where the weld is intended to form a hermetical seal.

In the case of a laser as an energy source, a method for processing may include: selecting a power, beam size, and movement speed for the laser to produce a predetermined result; focusing the laser on a subset of a predetermined portion of the shape memory material; and adjusting the spatial relationship of the laser and the shape memory material such that a beam from the laser contacts all of the predetermined portion of the shape memory material. In some cases, the laser may be operated in a pulsed fashion to provide shorter bursts of energy to control the application of energy.

The processing of shape memory materials, whether by laser heating or otherwise, are generally performed in the presence of a shielding gas, such as Argon or similar known production gas. Without the use of a shielding gas, the components or the shape memory material may react with oxygen or other elements to produce unwanted by-products or impurities; possibly resulting in the shape memory material having unwanted characteristics, such as weakness, brittleness, or the like.

Figure 2:
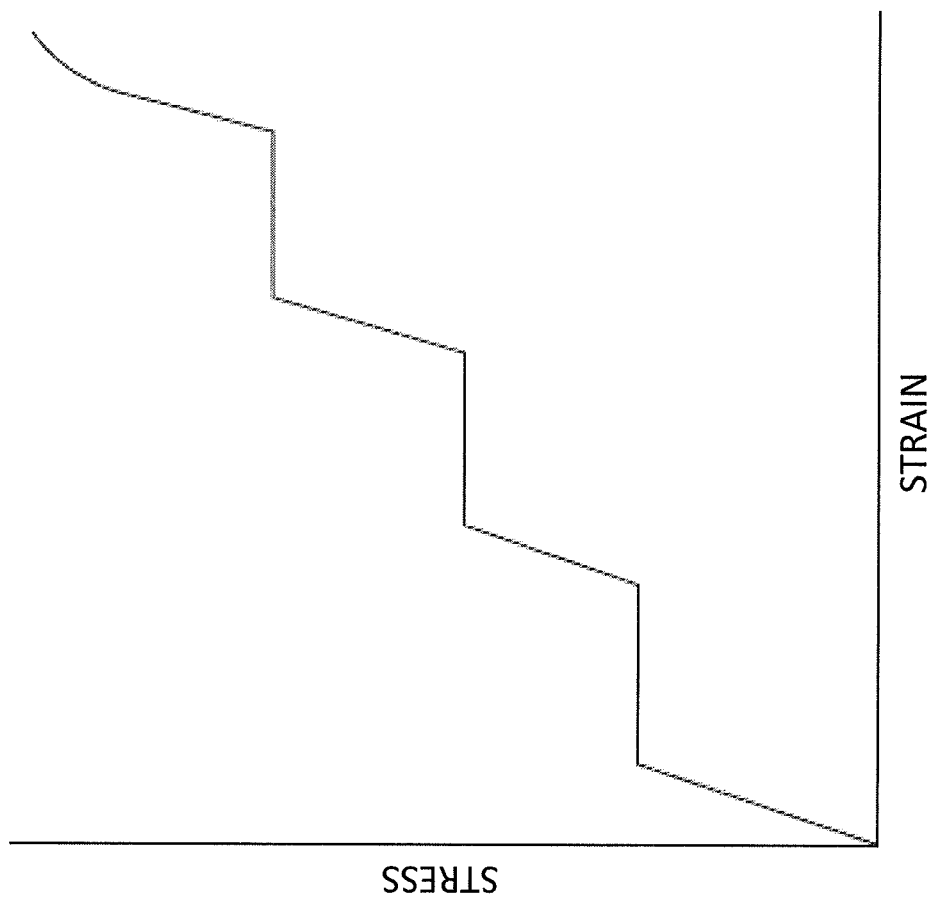
FIG. 2 illustrates the type of stress-strain curve expected for a strip of shape memory material having multiple transformation temperatures along its length.

It is an intended advantage that changing of the local chemistry of a shape memory material, according to the embodiments of the method herein, may also be used to produce a stress-strain curve for the shape memory material that reflects multiple pseudo-elastic regions. FIG. 2 illustrates the type of stress-strain curve expected for a strip of shape memory material having multiple transformation temperatures along its length. The unloading curve is expected to be similarly affected. As shown, for the loading curve, the material will be expected to exhibit multiple sequences of elastic deformation followed by a plateau of pseudo-elastic deformation. In this way, different areas of the shape memory material may have different elastic or pseudo-elastic properties than other areas of the shape memory material, which may remain in a non-elastic state.

It is also an intended advantage that changing of the local chemistry of a shape memory material according to embodiments of the method herein, may also be used to vary the hardness of the material. Areas where the local chemistry has been changed due to material having been vaporized may generally exhibit altered hardness with respect to areas where chemistry was not changed or areas where vaporization was not as extensive.

Further, the embodiments herein of treating/forming a workpiece of shape memory material may be used to produce a shape memory material having multiple force profiles. As described herein, changing of the local chemistry of a shape memory material may alter the force profile of material when the shape memory material is heated or otherwise transitions from the martensitic state to the austenitic state. If a load is applied to the shape memory material that resists the transition to the austenitic state, the shape memory material will counter that load with a force. The force profile of the shape memory material may be configured such that multiple areas of the shape memory material can provide different forces when a load is applied to the shape memory material. In some cases, using the systems, apparatuses and methods described herein, a multiple memory material (MMM) may be fabricated with a force memory having a spatial resolution of up to approximately 0.025 mm, and a force memory having a force resolution of up to approximately ±5 MPa. In other cases, the MMM may be fabricated with a force memory having a spatial resolution of up to approximately 0.5 mm, and a force memory having a force resolution of up to approximately ±10 MPa.

In some cases, during the processing of shape memory materials, additional elements may be added to change the properties of the MMM. In an example, Nitrogen or Hydrogen can be added to the area of the shape memory material that is intended to have the local chemistry altered in order to provide increased strength. In some cases, the additional elements may be added to the shielding gas, or as a filler material.

Figure 3:
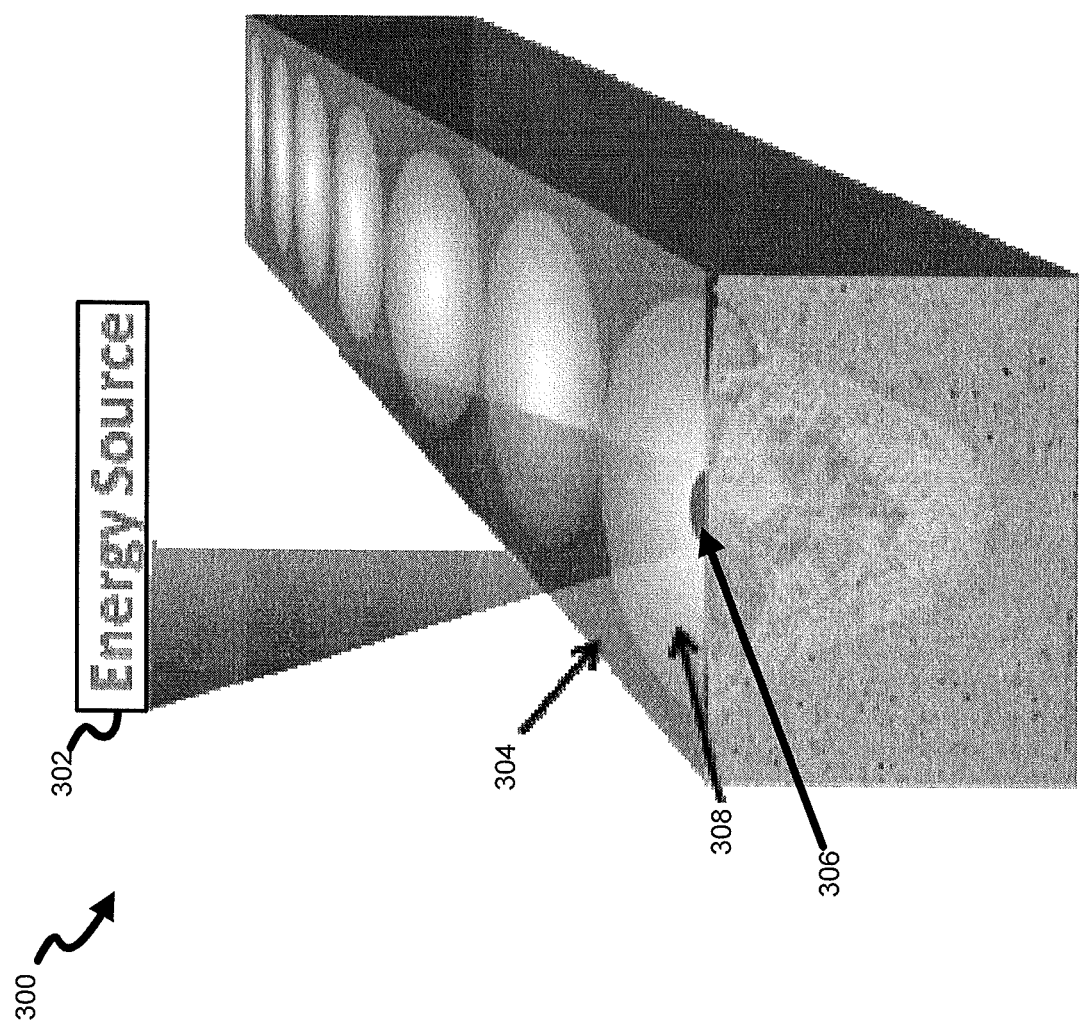
FIG. 3 illustrates a perspective view of an example application of an energy source to a shape memory material for fabrication of an MMM.

FIG. 3 illustrates a perspective view of an example application of an energy source to a shape memory material for fabrication of an MMM 300. As described herein, MMMs may be fabricated by applying energy from an energy source 302 to a region 306 of a shape memory material 304 in order to modify the local chemistry (including the atomic structure) of the shape memory material 304 in the region 306, and in some cases, in the area 308 surrounding the region 306 through conduction. In this example, the energy source 302 is a laser. The energy source 302 applies energy to the shape memory material 302 in a controlled fashion to produce predefined changes in the characteristics of the shape memory material 302. As described herein, due to the application of the energy source 302, the local shape memory, pseudo-elastic properties and/or force profile of the shape memory material 304 in the region 306 and surrounding area 308 can be precisely tuned to exhibit a desired functionality. In some cases, there may be a further heat affected region at the interface that may also be affected due to the processing and may further contribute towards the change in properties. This heat affected region may be proximate to or just outside the processed region at the perimeter. This capability is expected to be beneficial for a wide variety of applications ranging from health care to aerospace.

While FIG. 3 illustrates a shape memory material in the shape of a rectangular prism, the systems, apparatuses and methods described herein may work with a shape memory material having any suitable shape; for example, cylindrical, cuboid, triangular prism, polygonal prism, or the like. In a certain case, the shape memory material may be substantially planar; for example, provided in sheets of material. In further cases, the shape memory material may have recesses, depressions, hollows, cavities, or the like; for example, having a tubular shape, 'U' shape, dimpled shape, or the like.

FIGS. 4A to 4C illustrate cross-sectional views of a shape memory material having energy applied 400. It is an intended advantage that varying the penetration depth of energy applied to a region of a shape memory material 402 may produce different force profiles associated with how strongly each region resists not transitioning to the memory shape of the austenitic state when a load is applied. It is also an intended advantage that the transformation temperature may be changed or kept constant independent of the change in force profile through configuring, for example, the pulse frequency and/or the pulse duration of the energy source.

In the example of FIG. 4, the shape memory material 402 has a square cross section. Energy is applied to the top side of the shape memory material 402 with varying levels of energy penetration. In FIG. 4A, there is a region of energy penetration 404a in the shape memory material 402a. The local chemistry of the shape memory material 402a will be changed for approximately this region of the shape memory material 402a. In FIG. 4B, there is region of energy penetration 404b in the shape memory material 402b that is greater in size than the region of energy penetration 404a in FIG. 4A. Due to the larger region of energy penetration 404b resulting in more material vaporization, the shape memory material 402b of FIG. 4B may have a different force profile than the shape memory material 402a of FIG. 4A. In an example, where the shape memory material is nitinol, the shape memory material 402b of FIG. 4B will react with less force in response to a load than the shape memory material 402a of FIG. 4A. The shape memory material 402b of FIG. 4B may react with less force because at least some of the more volatile material, in this case Nickel, has vaporized in the region of energy penetration 404b and the nitinol now includes less material in the region of energy penetration 404b to resist not transitioning to the shape of the austenitic state when the load is applied.

In FIG. 4C, there is a region of energy penetration 404c in the shape memory material 402c that is greater in size than the region of energy penetration 404b in FIG. 4B. The region of energy penetration 404c reaches almost full penetration through the shape memory material 402c. When the level of energy penetration is higher, upon re-solidification of the shape memory material 402c, surface tension of the shape memory material 402c may cause the shape memory material 402c to resolidify into a spherical or semi-spherical shape for the region of energy penetration 404c. Hence, an energy source may be configured to provide energy penetration that is limited in such a way that the surface tension of the shape memory material retains a desired shape upon re-solidification. Where the cross-section of the shape memory material is spherical or semi-spherical, or where a spherical or semi-spherical re-solidification shape is desirable, the depth of energy penetration may not need to be limited due to concerns over re-solidification shape.

Figure 6:
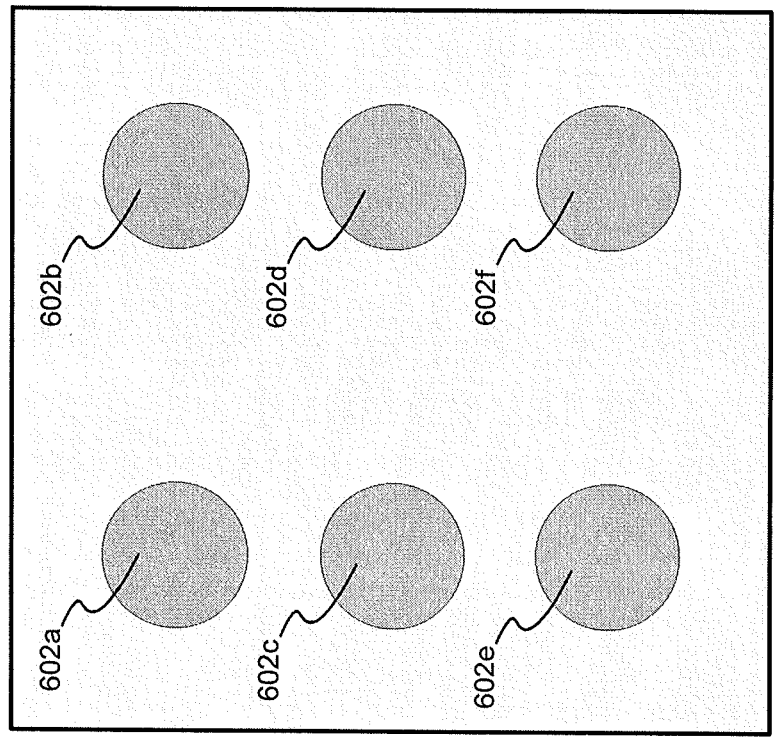
FIG. 6 illustrates a top view of an example shape memory material with a substantially planar shape.
Figure 5:
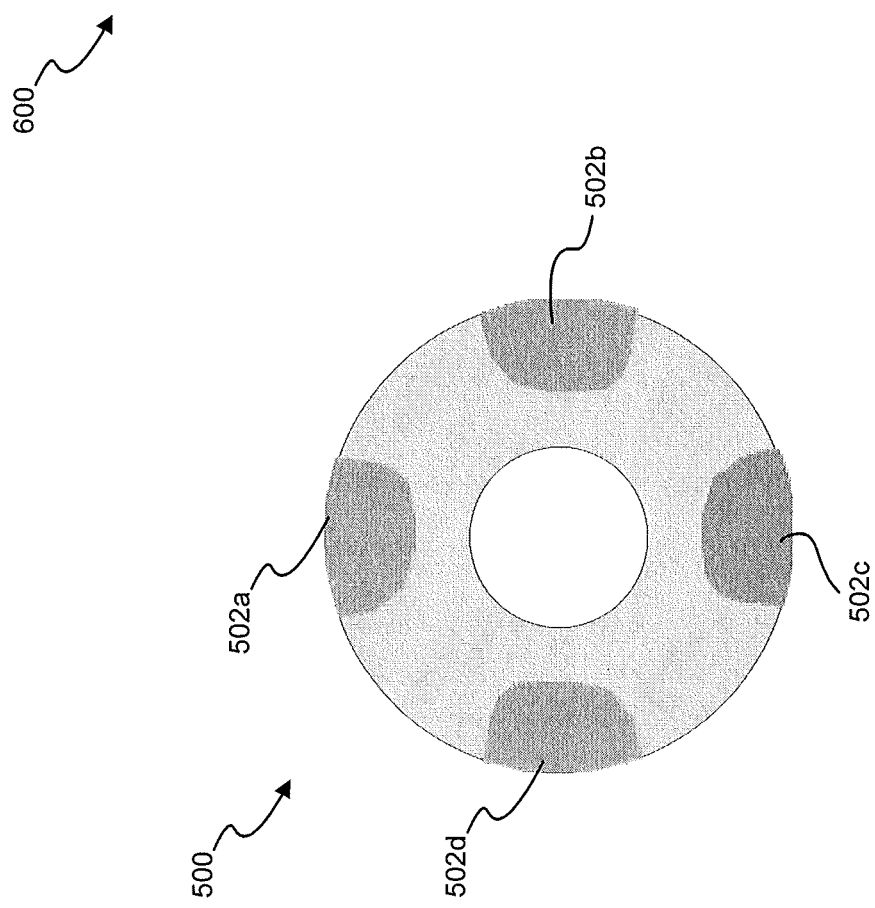
FIG. 5 illustrates a cross-sectional view of an example shape memory material with a tubular cross-section.

FIGS. 5 and 6 illustrate examples of shape memory materials with multiple energies applied. FIG. 5 illustrates a cross-sectional view of a shape memory material 500 with a donut-shaped cross-section. There are multiple, in this case four, regions of energy penetration 502a, 502b, 502c and 502d in the shape memory material 500. In other cases, there may be more or less than four regions of energy penetration depending on the size of the region of energy penetration 502 and the size of the shape memory material 500. Each region of energy penetration may be configured to have a different transformation temperature and/or force profile. In the example of FIG. 5, the shape memory material 500 cross-section is donut-shaped such that there is an inner cavity. An energy source may be configured to limit the region of energy penetration 502 such that the energy penetration does not reach the inner cavity. If the region of energy penetration 502 were to reach the inner cavity, upon re-solidification, the inner cavity may lose some structural integrity.

FIG. 6 illustrates a top view of a shape memory material 600 with a substantially planar shape. There are multiple, in this case six, regions of energy penetration 602a, 602b, 602c, 602d, 602e and 602f in the shape memory material 600. In other cases, there may be more or less than six regions of energy penetration spread-out over the face of the shape memory material 600 depending on the size of the region of energy penetration 602 and the size of the face of the shape memory material 600.

Figure 7:
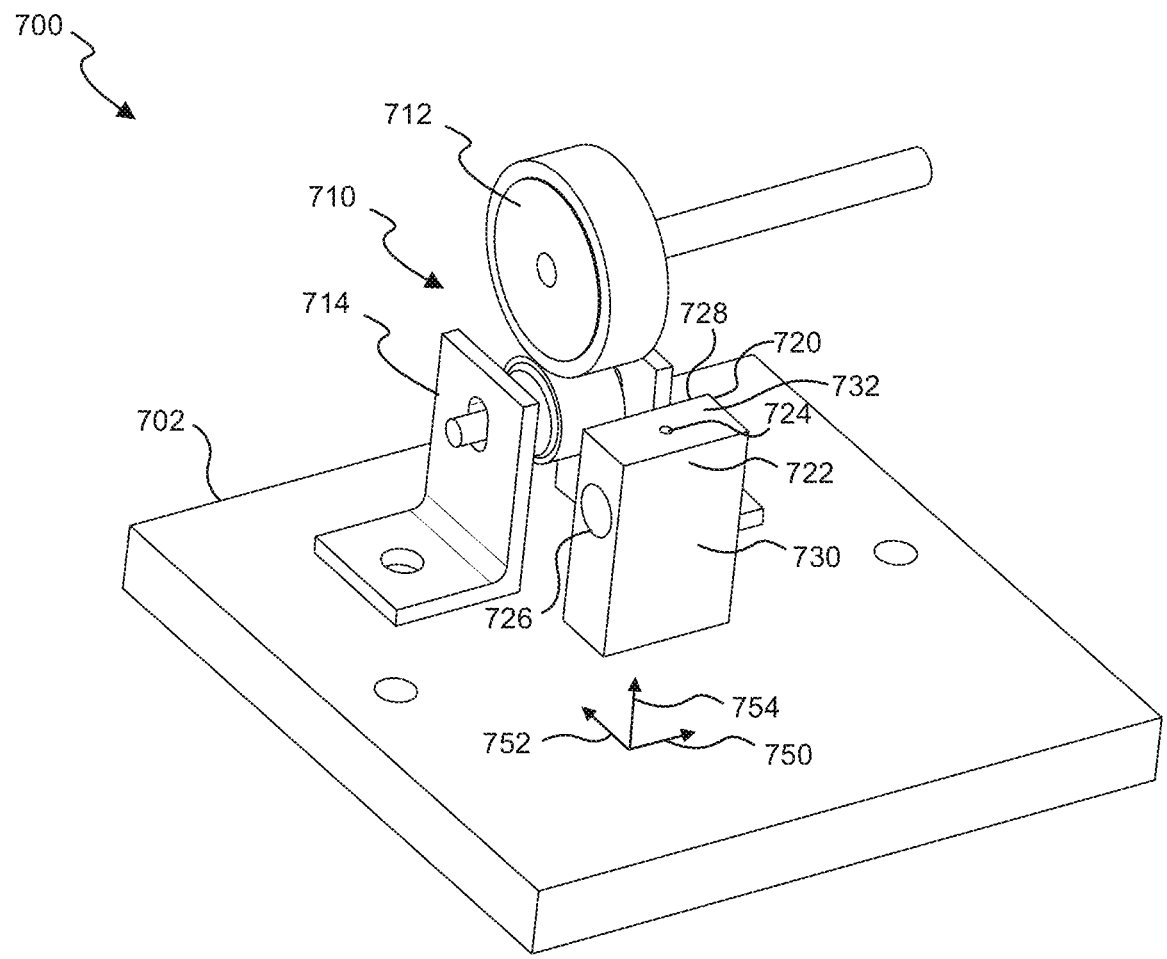
FIG. 7 illustrates a perspective view of an apparatus for fabrication of a MMM, according to an embodiment.
Figure 8C:
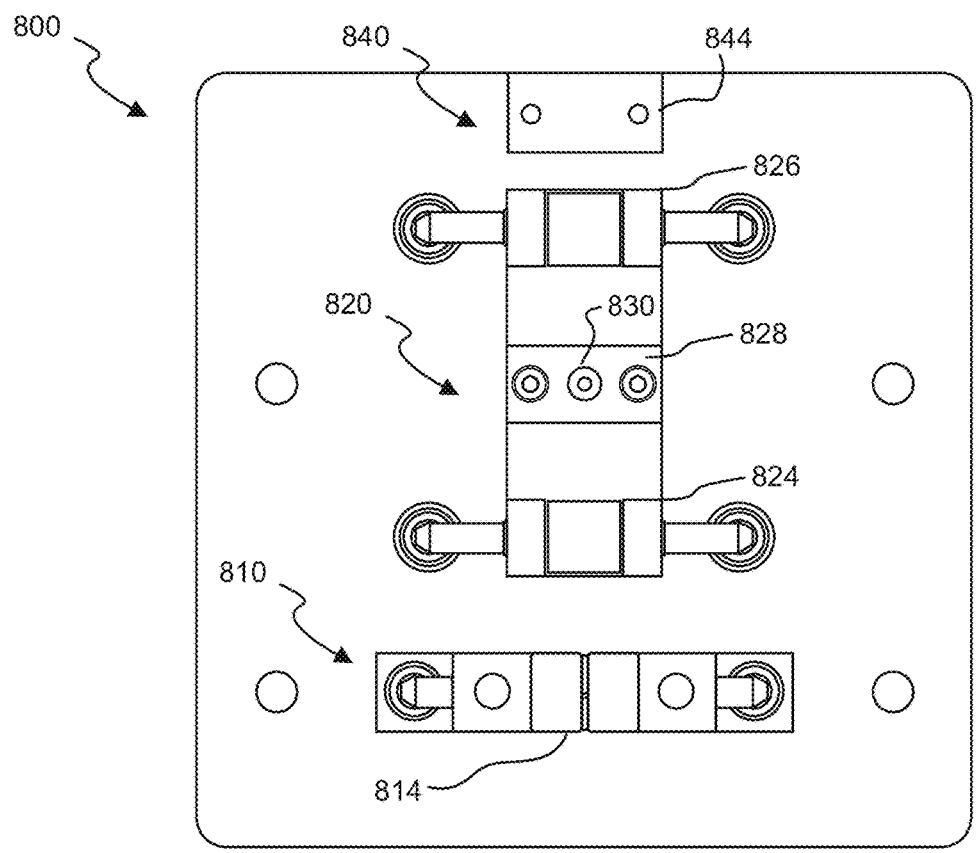
Figure 8D:
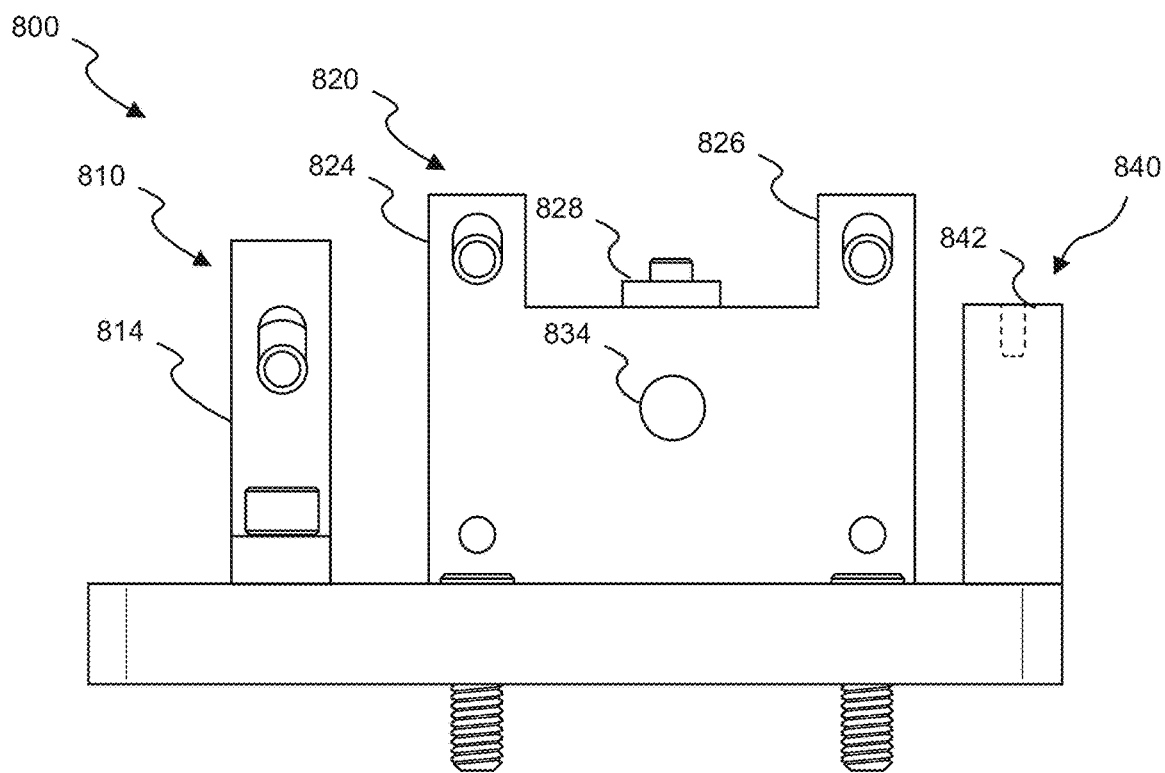
Figure 8E:
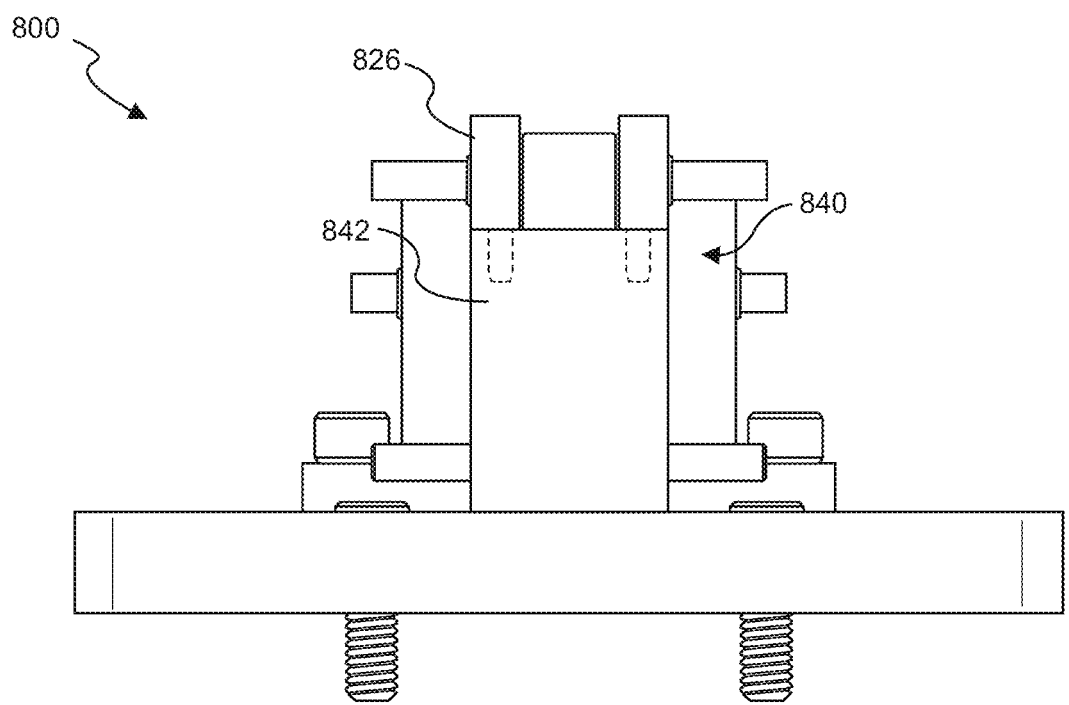
Figure 8F:
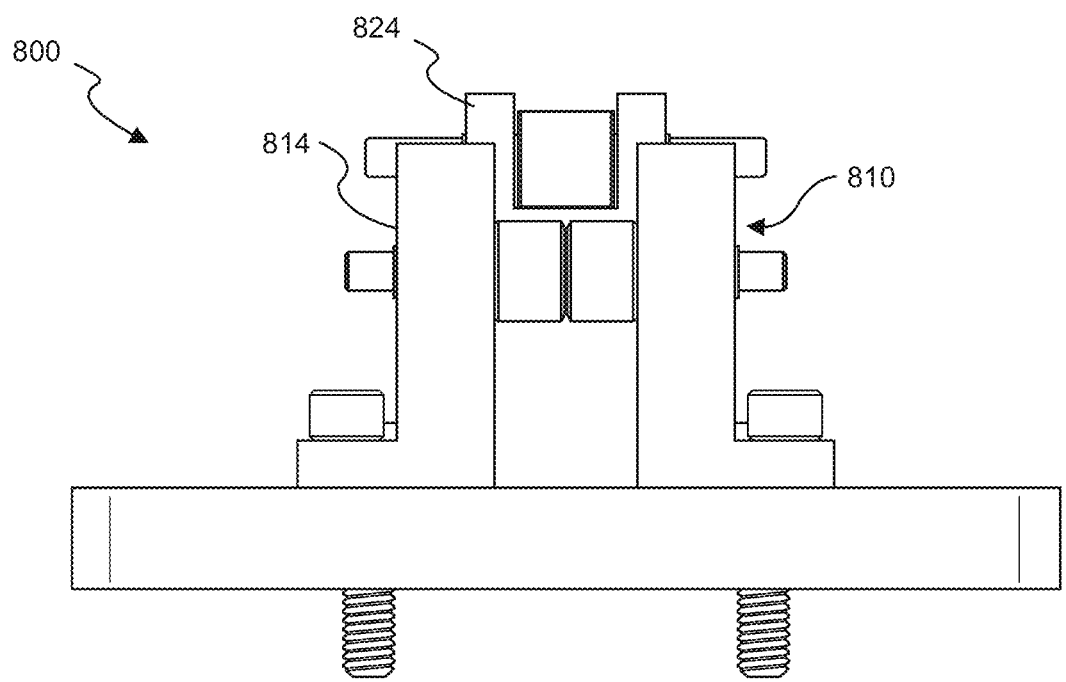

FIG. 7 illustrates a perspective view of an embodiment of an apparatus 700 for fabrication of a MMM having a long narrow shape such as a wire or the like. The apparatus 700 includes a base 702, a feeder assembly 710 and a processing station 720. The base 702 may be any suitable surface for supporting and maintaining proper alignment of the feeder assembly 710 and the processing station 720. In some cases, the base 702 may be omitted where the other components are already suitably mounted.

The feeder assembly 710 includes an upper roller assembly 712 and a lower roller assembly 714. The feeder assembly 710 receives the shape memory material, for example nitinol, between the upper roller assembly 712 and the lower roller assembly 714. In some cases, the shape memory material may be received by the feeder assembly 710 from a source of shape memory material; for example, a spool, a reel, a cassette, a mandrel, a box, or the like. The feeder assembly 710 may receive the shape memory material manually or through an automated process.

In a certain case, the upper roller assembly 712 may be driven by, for example, a motor (not shown) and the lower roller assembly 714 may be 'free spinning'. In other cases, the upper roller assembly 712 may be 'free spinning' and the lower roller assembly 714 may be driven, both upper roller assembly 712 and lower roller assembly 714 may be driven, or both upper roller assembly 712 and lower roller assembly 714 may be 'free-spinning'.

Upon receiving the shape memory material between the upper roller assembly 712 and the lower roller assembly 714, the upper roller assembly 712 rotates feeding the shape memory material to the processing station 720. The feeder assembly 710 may be configured to hold the shape memory material in tension as the shape memory material is fed to the processing station 720. Further, the feeder assembly 710 may include a mechanism to maintain alignment of the shape memory material with the processing station; for example, having an appropriately sized slot in the upper roller assembly 712 or the lower roller assembly 714. In a further example, the feeder assembly 710 may be replaced by any suitable mechanism for feeding the shape memory material to the processing station 720; for example, a robotic arm. In some cases, the source of shape memory material, for example, the spool, may be pre-tensioned to ensure tension is maintained by the feeder assembly.

The feeder assembly 710 feeds the shape memory material into the processing station 720. The processing station 720 includes a material passageway 722, an energy source aperture 724 and a shielding gas engagement portion 726. The material passageway 722 passes through the processing station 720 from an entrance at a front side 728 of the processing station 720, which faces the feeder assembly 710, to an exit at a rear side 730 of the processing station 720, opposite the feeder assembly 710. The material passageway 722 aligns with the upper roller assembly 712 and the lower roller assembly 714. The material passageway 722 is typically configured in size and shape to accept the particular shape memory material being processed so that there is no or only smaller amounts of out-flow of shielding gas through the material passageway 722.

The shape memory material is fed from the feeder assembly 710 to the entrance at a front side 728 of the processing station 720. As the feeder assembly 710 feeds shape memory material, the shape memory material is passed through the material passageway 722 until it emerges at the exit of the material passageway 722. While the shape memory material passes through the material passageway 722, the shape memory material is processed into an MMM 200, as described herein. The feeder assembly 710 may feed the shape memory material continuously, stepped, or as generally required for processing. The shape memory material may be fed either by the feeder assembly pushing the material for processing, or the shape memory material may be pulled through the processing station, by for example, a guiding assembly within the processing stations or a separate guiding assembly. In one example, the shape memory material may be fed at 0.5 mm/sec in a stepped manner such that the material is fed 0.5 mm, processed, then moved another 0.5 mm and processed, and so forth. This stepped process may be particularly useful where a larger portion of the material is being treated and tension during treatment might cause the material to separate. It will be understood that the length of the movement and the speed of the movement may be varied depending on the size of the area being processed and the material being used.

The energy source 910 (in FIG. 9) is applied to the shape memory material through the energy source aperture 724. In some cases, a plurality of energy sources may be provided and may be applied through a plurality of energy source apertures. The energy source aperture 724 is located on a top side 732 of the processing station 720 and is formed such that the bottom of the energy source aperture 724 intersects with the material passageway 722. Generally speaking, the energy source aperture 724 provides a direct line of sight between the energy source 910 and the shape memory material as the shape memory material passes through the material passageway 722. The energy source aperture 724 may vary in size and shape depending on the type of energy source being used and the size and shape of the shape memory material being processed. In some cases, after passing through the material passageway 722, the shape memory material, having been fabricated into a MMM, is placed into or onto a receptacle; for example, a spool, mandrel, container, or the like. It will be understood that, in some cases, the energy source may be to a side of the processing station and the energy source aperture 724 may be located on a side of the processing station.

As indicated above, the fabrication of an MMM 200 is generally performed in the presence of a shielding gas, such as Argon or an appropriate non-reactive production gas. The shielding gas is provided to the processing station 720 via the shielding gas connector 726 sometimes referred to as the shielding gas engagement portion. In the example of FIG. 7, the opening of the shielding gas connector 726 is located on a lateral side of the processing station 720; however, the shielding gas connector 726 may be located on any suitable part of the processing station 720. The shielding gas connector 726 is configured such that shielding gas is provided to the intersection of the energy source aperture 724 and the material passageway 722. In some cases, the shielding gas connector 726 may have a coupling at its opening to connect with a hose that supplies the shielding gas; for example, having a hose barb, screw engagement, clamp ring, or the like.

In further embodiments, the feeder assembly 710, instead of feeding the shape memory material to the material passageway 722, may pull the shape memory material as it exits the material passageway 722 or move the shape memory material in both directions, back and forth, as required for processing.

FIGS. 8A to 8F illustrate other embodiments of an apparatus 800 for fabrication of a long narrow MMM, such as a wire. The apparatus 800 for fabrication of a MMM includes a base 802, a feeder assembly 810, a processing station 820 and an alignment guide 840. The base 802 may be any suitable surface for supporting and maintaining proper alignment of the feeder assembly 810, the processing station 820 and the alignment guide 840. In some cases, the base 802 may be omitted where the other components are already suitably mounted.

Similar to the embodiment of FIG. 7, the feeder assembly 810 includes an upper roller assembly 812 and a lower roller assembly 814. The feeder assembly 810 receives the shape memory material, for example nitinol, between the upper roller assembly 812 and the lower roller assembly 814. In some cases, the shape memory material may be received by the feeder assembly 810 from a source of shape memory material; for example, a spool, a reel, a cassette, a mandrel, a box, or the like. In certain cases, the upper roller assembly 812 may be driven by, for example, a motor (not shown) and the lower roller assembly 814 may be free spinning. In other cases, the upper roller assembly 812, the lower roller assembly 814, or both, may have a slot for receiving and guiding the shape memory material such that the shape memory material maintains proper alignment with the processing station 820. The upper roller assembly 812, the lower roller assembly 814, or both, may be composed of a resilient material, for example steel, or a malleable material, for example rubber.

Upon receiving the shape memory material between the upper roller assembly 812 and the lower roller assembly 814, the upper roller assembly 812 rotates feeding the shape memory material to the processing station 820. In further embodiments, the feeder assembly 810 may be any suitable mechanism for feeding the shape memory material to the processing station 820; for example, a robotic arm. In some cases, the feeder assembly 810 may operate in both directions as required for fabrication of the MMM.

The processing station 820 includes a body 822, a first roller 824, a second roller 826, a processing cap 828 and a shielding gas engagement portion 834. The shape memory material is fed from the feeder assembly 810 to the processing station 820 where the shape memory material passes under the first roller 824. The first roller 824 and the second roller 826 may be used to guide the shape memory material to and from the processing cap 828 such that the shape memory material remains level and moves stably during processing. As well, the first roller 824 and the second roller 826 may ensure that the shape memory material remains at an appropriate feeding tension to maintain the shape memory material in the correct position and orientation as the shape memory material passes through the processing cap 828. In some cases, the upper roller assembly 812 may push or pull the shape memory material and rollers 824 and 826 help align and push the shape memory material.

After the first roller 824, the shape memory material enters the processing cap 828. The processing cap 828 includes a material passageway 832 that passes through the processing cap 828 or between the processing cap 828 and the body 822. The processing cap 828 also includes an energy source aperture 830. The processing cap 828 is mounted to the top of the body 822 using, for example a fastener, epoxy, or the like. In some cases, the processing cap 828 may be integral with the body 822. The energy source aperture 830 is located on a top side of the processing cap 828 and is positioned such that the bottom of the energy source aperture 830 intersects with the material passageway 832.

The shape memory material passes through the material passageway 832 of the processing cap 828. The material passageway 832 is configured in size and shape to accept the shape memory material. As the shape memory material passes through the material passageway 832, an energy source acts on the shape memory material through the energy source aperture 830. When the energy source acts on the shape memory material according to the processing parameters, the shape memory material is fabricated into a MMM, as described herein.

The shielding gas connector 834 may be mounted on a side of the body 822. In some cases, the shielding gas connector 834 may have a coupling at its opening to connect with a hose that supplies the shielding gas; for example, having a hose barb, screw engagement, clamp ring, or the like.

The body 822 has an opening at the connection of the shielding gas engagement portion 834. The body 822 also has an opening underneath the energy source aperture. Within the body 822, there is an interior passageway which connects the opening underneath the energy source aperture 830 to the opening at the shielding gas engagement portion 834. Thus, shielding gas supplied to the shielding gas engagement portion 834 traverses the interior passageway of the body 822 such that shielding gas is provided to the energy source aperture 724.

After the shape memory material is fabricated into an MMM and exits the material passageway 832 of the processing cap 828, the shape memory material passes under the second roller 826 and through the guidance assembly 840. The second roller 826 may be used to guide the shape memory material as the shape memory material exits the processing cap 828; such that the shape memory material remains level and moves stably. The first roller 824 and second roller 826 may be composed of a resilient material, for example steel, or a malleable material, for example rubber. The first roller 824 and second roller 826 may include a slot to further guide the shape memory material. In some cases, the apparatus 800 may omit the first roller 824 and/or the second roller 826 if enough guidance of the shape memory material is provided by the processing cap 820. In further cases, the first roller 824 and/or the second roller 826 may be replaced by a different guidance mechanism; for example, a slotted plate.

The guidance assembly 840 includes a base 842 and a guidance cap 844. The guidance cap 844 is located on the top of the base 842 and includes a guidance passageway 846. The shape memory material passes through the guidance passageway 846 after passing under the second roller 826 and is intended to provide stable guidance of the shape memory material, for example, to ensure that the shape memory material is not bent after exiting the material passageway 832. In some cases, the guidance cap 844 may be similar to the processing cap 820. In further cases, the guidance assembly 840 may be omitted if the shape memory material is sufficiently guided after exiting the processing cap 828. In other cases, the guidance assembly 840 may be replaced by a different guidance mechanism; for example, an assembly similar to the feeder assembly 810 or the like. In some cases, after passing through the guidance passageway 846, the shape memory material, having been fabricated into a MMM, is placed into a receptacle; for example, a spool, mandrel, container, or the like. In some cases, the rigidity of the shape memory material may be sufficient to guide the material through the system.

Figure 9:
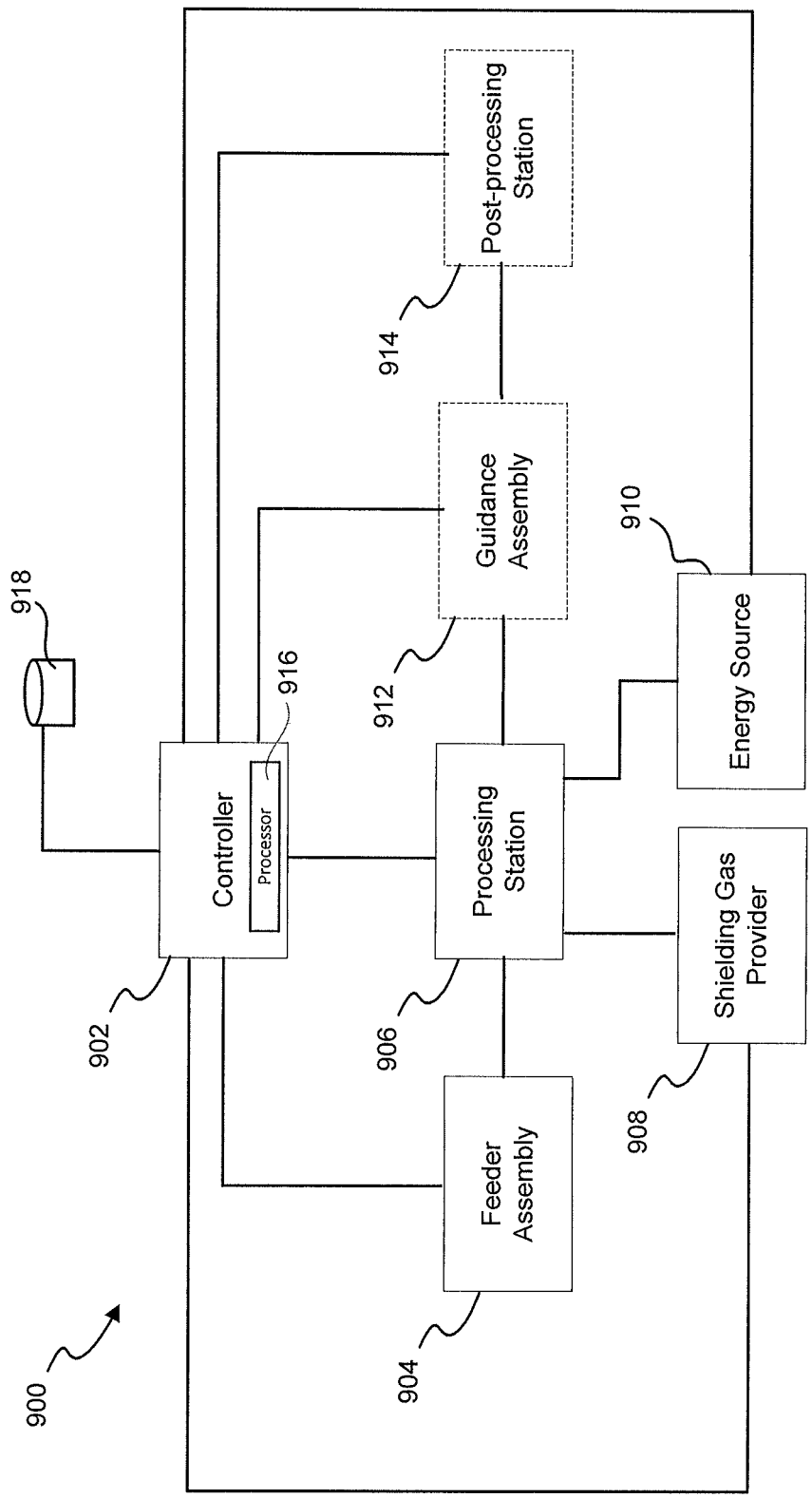
FIG. 9 illustrates a block diagram of a system for fabrication of a MMM, according to an embodiment.

FIG. 9 illustrates a block diagram of an embodiment of a system 900 for fabrication of a MMM. The system 900 includes a controller 902, a feeder assembly 904, a processing station 906, a shielding gas provider 908, an energy source 910, a guidance assembly 912 and, in some cases, a post-processing station 914. The controller 902 may control the fabrication of the MMM by directing and coordinating the operation of the other components of the system 900. The controller 902 may include a processor 916, a microcontroller, or the like. The controller 902 may be connected to a network; for example, a local area network (LAN), the Internet, or the like. The controller 902 may also be operatively connected to a memory component, for example a database 918 where the controller may store and retrieve data, for example, processing parameters or the like.

Figure 10:
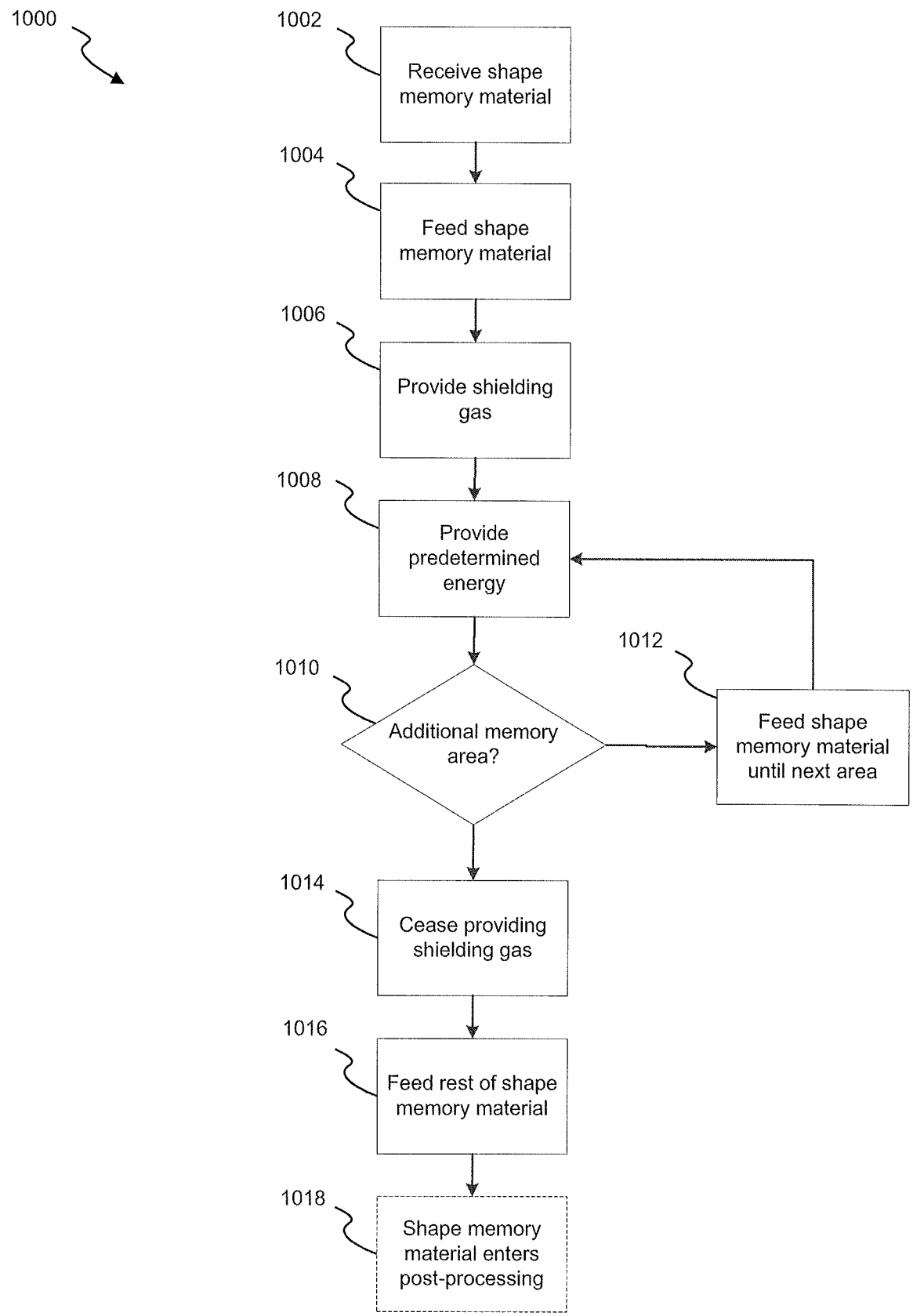
FIG. 10 is a flowchart of a method for fabricating a MMM, according to an embodiment.

The components of the system 900 will be described in relation to FIG. 10, a flowchart of an embodiment of a method for fabricating a MMM 1000. At 1002, the feeder assembly 904 receives the shape memory material from a source of shape memory material; for example a spool, a reel, a cassette, a mandrel, a box, or the like. The shape memory material may be manually or automatically loaded into the feeder assembly 904.

At 1004, the feeder assembly 904 receives instructions from the controller 902 to feed the shape memory material to the processing station 906. The feeder assembly 904 may feed a predetermined length of shape memory material into the processing station 906 such that a predetermined section of the shape memory material is located in the region of the material passageway 722 or 832 under the energy source aperture 724 or 830.

At 1006, the controller 902 directs the shielding gas provider 908 to provide shielding gas to the shielding gas connector 726 or 834 prior to processing of the shape memory material. A sufficient amount of shielding gas may be provided by the shielding gas provider 908 to ensure that the section of the shape memory material located under, and approximate to, the energy source aperture 724 or 830 is enveloped in shielding gas. In some cases, the processing station 906 may include a sensor(s) to determine the level of shielding gas proximate to the energy source aperture 724 or 830. In some cases, the gas flow rate may be determined via computational fluid dynamics to determine when sufficient shielding gas has been received by the processing station.

At 1008, the controller 902 activates the energy source 910 to apply energy to the shape memory material through the energy source aperture 724 or 830 of the processing station 906 according to the predetermined parameters. An area of the shape memory material located under the energy source aperture 724 or 830 thus receives energy such that at least some melting and vaporization occurs (based on the temperature and partial pressures at the local area). As described herein, the energy source 910 provides a predetermined energy to the shape memory material such that the local area of the shape memory material exhibits a predetermined memory.

At 1010, the controller 902 determines whether there are additional memory areas of the shape memory material to be created. If there are additional memory areas to be created, at 1012, the controller 902 instructs the feeder assembly to feed the shape memory material to the processing station 906 until the next area of the shape memory material to be given a memory is located under, and/or proximate to, the energy source aperture 724 or 830. Then, at 1008, the energy source provides a predetermined energy to the new area of the shape memory material such that it exhibits a predetermined memory.

If there are no additional memory areas to be created, at 1014, the shape memory material is fabricated into a MMM and the controller 902 directs the shielding gas provider 908 to cease providing the shielding gas to the processing station 906. In some cases, the shielding gas will cease after each provision of energy from the energy source 910 at 1008 and only start again if, at 1012, a next area of the shape memory material to be given a memory is fed into the processing station 906.

At 1016, the controller 902 directs the feeder assembly 904 to feed the remaining shape memory material through the processing station 906. In some cases, after the shape memory material exits the processing station 906, the shape memory material is guided by a guidance assembly 912. The guidance assembly 912 may be passive (for example, a slotted plate, a 'free spinning' roller, or the like), active (for example, a motorized roller assembly, robotic arm, or the like), or both. If the guidance assembly 912 is active, the guidance assembly 912 may receive instructions from the controller to coordinate with the feeder assembly 904 and the processing station 906.

At 1018, in some cases, after the shape memory material has been fabricated into an MMM, the MMM may have post-processing applied in the post-processing station 914, which may be controlled by the controller 902. In some cases, post-processing may include cutting and shaping the MMM into a desired size and form. In other cases, the post-processing may include cleaning and/or polishing the MMM. In yet other cases, the post-processing may include wire drawing to reduce the cross-section of the MMM by pulling the MMM through one or more drawing dies. In yet other cases, the post-processing may include affixing or attaching multiple MMMs together in a predetermined matter through, for example, welding, applying epoxy, using fasteners, or the like. In yet other cases, the post-processing may include cold-working the MMM to strengthen and/or shape the material by intentionally inducing deformation. In yet other cases, post-processing may include heat treating the MMM to achieve a desired result; for example, hardening, softening, tempering, shape forming, or the like. In yet other cases, post-processing may include allowing the MMM to undergo controlled in-situ cooling. In yet other cases, post-processing may include passing the MMM through a bath in order to remove any unwanted residuals on the MMM, for example, to remove acid, chemical agents, or the like. In yet other cases, post-processing may include oxide treatments of the MMM to increase breakdown potential of the MMM.

In further cases, after post-processing at the post-processing station 914, the MMM may be provided once again to the feeder assembly 904, at 1002, for further processing at the processing station 906. The processing at the processing station 906 and post-processing at the post-processing station 914 may be repeated as many times as necessary.

Figure 11:
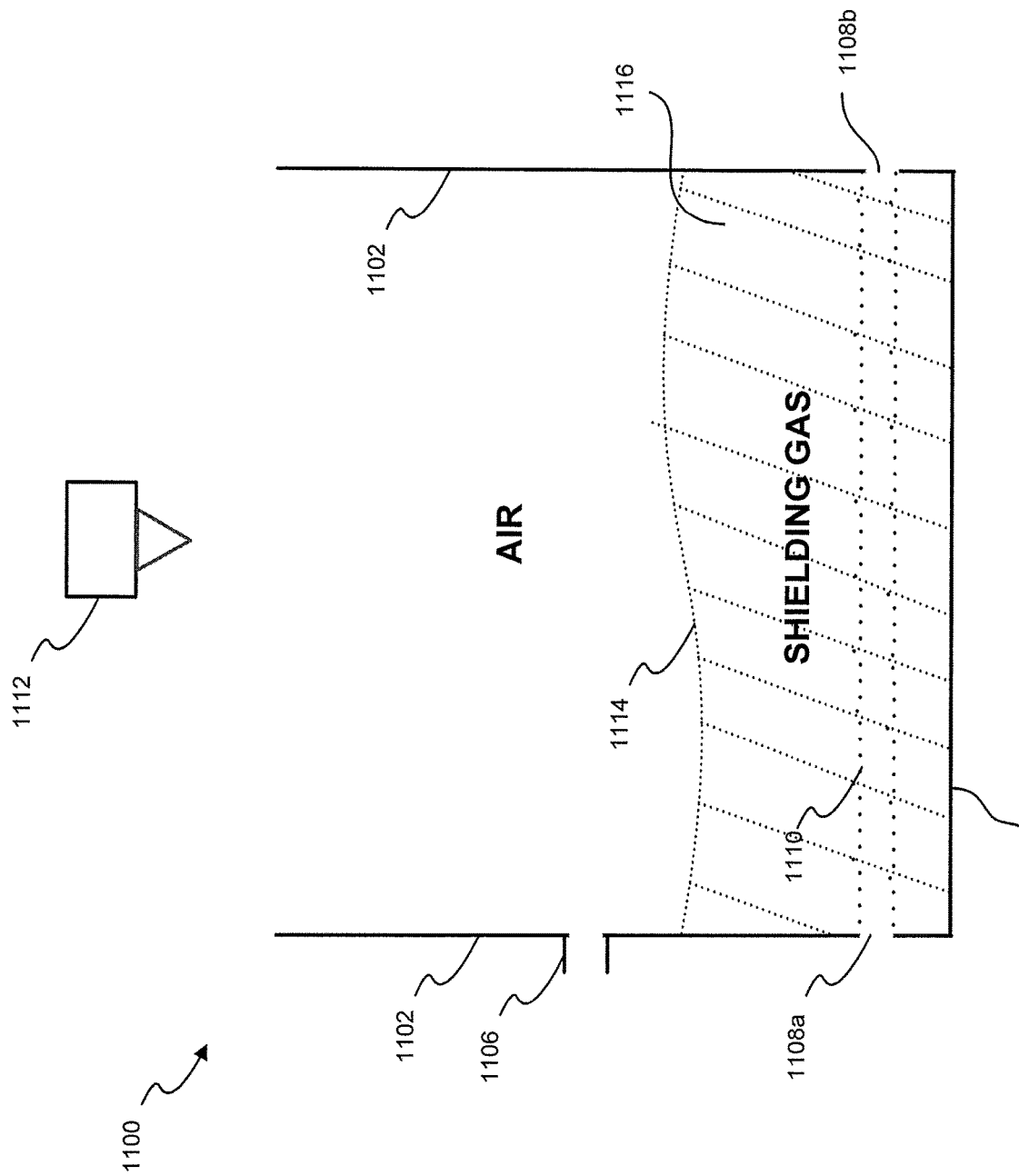
FIG. 11 illustrates a side view of a processing station, according to another embodiment.

Turning to FIG. 11, a cross-sectional side view of another embodiment for a processing station 1100 is shown. In this embodiment, the processing station 1100 is in a "bucket-shape" or in a "box-shape"; whereby the processing station has a bottom 1102, one or more sides 1104, and an opening at the top 1105 (an energy source aperture). A shielding gas engagement portion 1106 is located on the side 1102 or on the bottom 1104 of the processing station 1100. In some cases, the shielding gas engagement portion 1106 may have a coupling at its opening to connect with a hose; for example, having a hose barb, screw engagement, clamp ring, or the like.

Shielding gas 1116 is provided to the processing station 1100 through the shielding gas engagement portion 1106. For this embodiment of the processing station 1100, the shielding gas may be selected to be heavier than the ambient air around the processing station 1100; for example, argon. As the shielding gas 116 is heavier than the ambient air, the shielding gas 1116 supplied to the shielding gas engagement portion 1106 sinks to the bottom of the processing station 1100 and the ambient air is above the shielding gas 1116. In further cases, the shielding gas engagement portion 1106 may be omitted and the shielding gas may be supplied through the opening at the top of the processing station 1100.

The processing station 1100 includes a first opening 1108a and a second opening 1108b. The openings 1108 are located on opposing sides 1102 of the processing station 1100. The openings 1108 form a material passageway 1110 which the shape memory material passes through. The openings 1108 are configured in size and shape to accept the shape memory material. The shape memory material enters the first opening 1108a, passes through the processing station 1100 and exits through the second opening 1108b.

An energy source 1112 is located above the opening 1106. As the shape memory material passes through the processing station, the energy source 1112 provides a predetermined energy to the shape memory material such that the local area of the shape memory material exhibits a predetermined memory, as described herein. Since the shape memory material passes through the processing station 1100 below the boundary 1114 of the ambient air with the shielding gas 1116, the shape memory material is enveloped in the shielding gas 1116 while being acted on by the energy source.

In further embodiments of the processing station, there may be more than one energy source to provide energy to the shape memory material. Correspondingly, there may be an equal number of energy source apertures in the processing station positioned to accept energy from one of the energy sources. In some cases, each of the plurality of energy sources may be positioned to act on a different side of the shape memory material. In other cases, more than one of the energy source may be positioned to act on the same side of the shape memory material; particularly where the shape memory material has a rectangular or planar face or is a sheet format. Where there are multiple energy sources, all the energy sources may be configured to act at the same time or at overlapping times. In other cases, the energy sources can be configured to act at different times, or during different intervals of time, to, for example, provide progressive processing of the shape memory material.

In other embodiments, the processing station and/or the base may include structure for providing manual or automatic translational movement. As illustrated in FIG. 7, the translational movement can be along the X axis 750, the Y axis 752, the Z axis 754, or a combination of all axes. In some cases, the processing station, the base, or both, may include a track, castors, or the like in order to provide translation along the X axis 750 and/or Y axis 752. It is an intended advantage that translation along the X axis 750 and/or Y axis 752 may be used to precisely align the material passageway 722, 832, 1110 with the feeder assembly 710, 810. It is also an intended advantage that translation along the X axis 750 and/or Y axis 752 may be used to precisely position the region of the shape memory material to be processed under the energy source.

In other cases, the processing station, the base, or both, may include a lift, hoist, track, pulley, or the like to provide translation along the Z axis 754. It is an intended advantage that translation along the Z axis 754 may be used to precisely align the material passageway with the feeder assembly. It is a further intended advantage that, particularly where the energy source is a laser, translation along the Z axis 754 may be used to, for example, precisely focus the laser on a region of the shape memory material to receive the energy. Translational movement may be preferred in order to properly process a surface along both an X axis and a Y axis. In some cases, the surface may protrude or have crevices, for example a rounded surface, and Z axis control may also be processed.

It will further be understood that the systems and methods described above may be modified appropriately for processing of other formats of shape memory material, including sheets of material feeding through a slot in a similar way that the wire is feed through a hole in the above systems.

The systems, apparatuses and methods described herein are intended to provide a compact processing station that is at least partially enclosed such that shielding gas may be used without requiring an operator to use a sealed workstation. Thus, the systems, apparatuses and methods described herein are intended to increase production, reduce the space required for processing and reduce the costs associated with fabrication. Further, as the systems, apparatuses and methods described herein may use a controller or processor to automate the processing and fabrication of the MMM, the systems, apparatuses and methods described herein are intended to speed up fabrication of the MMM, increase output and reduce labor costs.

A MMM, and in particular, one made using the processes described herein, is intended to have application in a wide variety of areas, including providing improved functionality in existing devices and, in some cases, enabling the development of devices that may not have been possible using conventional technology.

Systems, apparatuses and methods described herein can be useful in the field of orthodontic archwires. Archwires may be used in orthodontic braces and other orthodontic applications in order to provide an operational force. Conventional orthodontic approaches typically require that archwires be replaced when a different force is desired. Repeated replacement increases costs for the patient as they have to pay for the new archwires and for the dental services required to replace the archwire. Also, the initial treatment using an archwire can be unpleasantly painful as the initial treatment typically uses a forceful archwire that acts on the patient's teeth and gums.

Using MMMs as an archwire is intended to enable more precise programmability of force along the length of the archwire. It is an intended advantage that having different force profiles along the length of the archwire may be desirable due to the ability to have different forces act on different areas of teeth.

Figure 12:
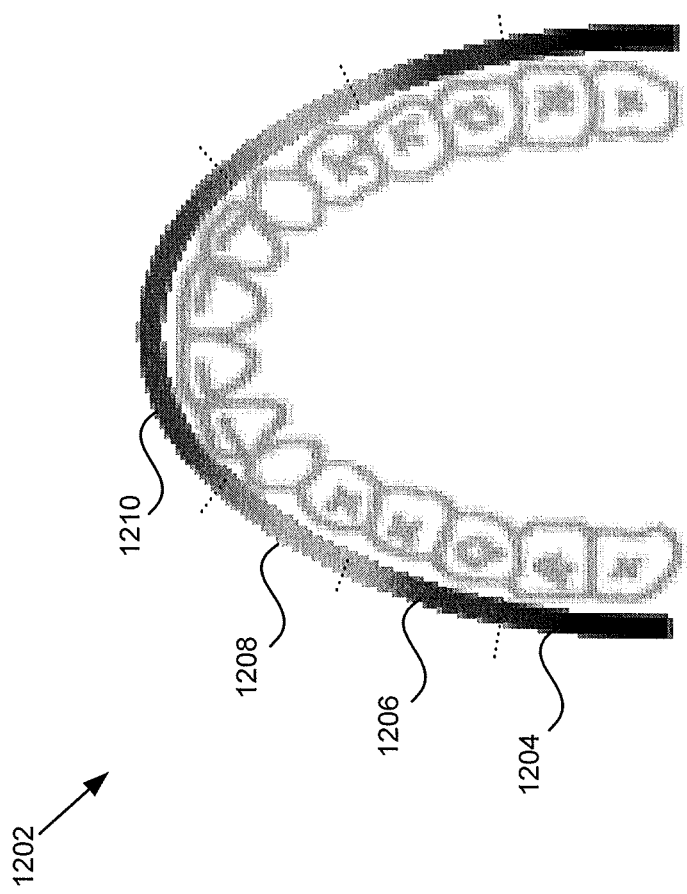
FIG. 12 illustrates an example force profile for an archwire using MMM.

In an example, fabrication of the MMM archwire may involve tuning each of the forces along the arch such that the force profile is lowest near the incisors and highest at the molars. An experiment was conducted in which force testing for both round archwire cross-sections (for example, 0.014" and 0.018") and square archwire cross-sections (for example, 0.014"×0.025" and 0.018"×0.025"). FIG. 12 illustrates an example force profile for an archwire 1202 in which the tensile forces of the MMM 1202 are configured to achieve a posterior force region 1204 of 160 MPa, 90 MPa between the posterior force region 1204 and the anterior force region 1210 with 60 MPa force at the anterior. In the example of FIG. 12, the archwire 1202 is processed to exhibit four distinct forces with the unprocessed shape memory material exhibiting the highest force. The archwire may include two distinct interior regions, with a first interior region 1206, proximate to to the posterior force region, having a force of approximately 140 MPa, and a second interior region 1208, proximate to the anterior force region, and having a force of approximately 90 MPa. In this example, processing may be conducted at a spatial resolution of 0.05 mm, which is intended to be acceptable to enable force tuning between a pair of teeth (typically 1.5 mm apart).

Compared with conventional archwire material, target forces are intended to be accurately achieved with minimal change to the loading and unloading curve characteristics. Compared with conventional archwire material, the force is more consistent and tuneable to desired magnitudes.

Testing was conducted on the MMM archwire by emulating the forces experienced by each individual tooth in the human mouth at body temperature. This may be achieved by using individual load cells that measure both horizontal and vertical forces as the emulated teeth move. From this, the maximum and minimum forces experienced in each direction can be quantified and compared. In some cases, suitable force profiles may be used which are typically dictated by the nature of the orthodontic work. The distance between the force values represents the relative force gradient. The magnitude of the vertical force of the conventional archwire is intended to be decreased. Similarly, frictional forces are also intended to decrease in the MMM archwire as compared to conventional archwire.

When also compared with conventional archwire, the MMM archwire's ability to spatially control the force along an arch appears to enable greater flexibility for the force profile of the archwire.

Further, a corrosion performance evaluation of MMM archwire shows that the MMM archwires are robust enough to withstand the corrosive environments typically experienced in a human mouth. Long-term nickel ion release for nitinol MMM archwire was measured in an artificial saliva solution incubated at body temperature. The corrosion performance evaluation revealed the MMM archwires to be acceptable for clinical application since the inherent archwire material remains substantially unchanged.

Using MMM archwire, a pre-torque archwire that applies a torque force labially or lingually at the anterior of the upper arch may be fabricated. The high forces experienced with conventional archwires often result in patient discomfort, which orthodontists typically constantly need to correct. However, due to the complex geometry of archwire, methods to precisely lower the torque force are conventionally not practical. In contrast, the resolution and process flexibility offered by MMM archwire may be able to provide more manageable forces for the patient. Using MMM archwire, there may be controllable decreases in the amount of torque applied by the archwire, which may be activated when the MMM archwire reaches a transformation temperature approximately equivalent to body temperature. Variable forces of pre-torque MMM archwires may be fabricated which may result in greater patient comfort and reduce patient clinical visits.

Systems, apparatuses and methods described herein can also be useful in the field of endodontic files or reamers. FIG. 13 illustrates a side view of an endodontic file 1700 using MMM. The endodontic file includes a handle 1702 and a filing wand 1704. The filing wand 1704 may include multiple abrasion points 1706 along its length. Endodontic files and reamers are used for multiple purposes, but particularly for cleaning and shaping a patient's root canal. It is generally preferable for endodontic files to adapt three-dimensionally to the shape of a given root canal. An endodontic file or reamer fabricated from MMM, such an MMM wire, may enhance the adaptation of the endodontic file by controlling the flexibility of the filing wand 1704 portion. Having a filing wand 1704 with different pseudo-elastic properties, and thus flexibilities, along its length may increase the adaptation of the filing wand 1704 to the shape of the root canal, while not being so malleable as to reduce the ability of the endodontic file 1700 to remove material from the root canal.

Figures 14A, 14B:
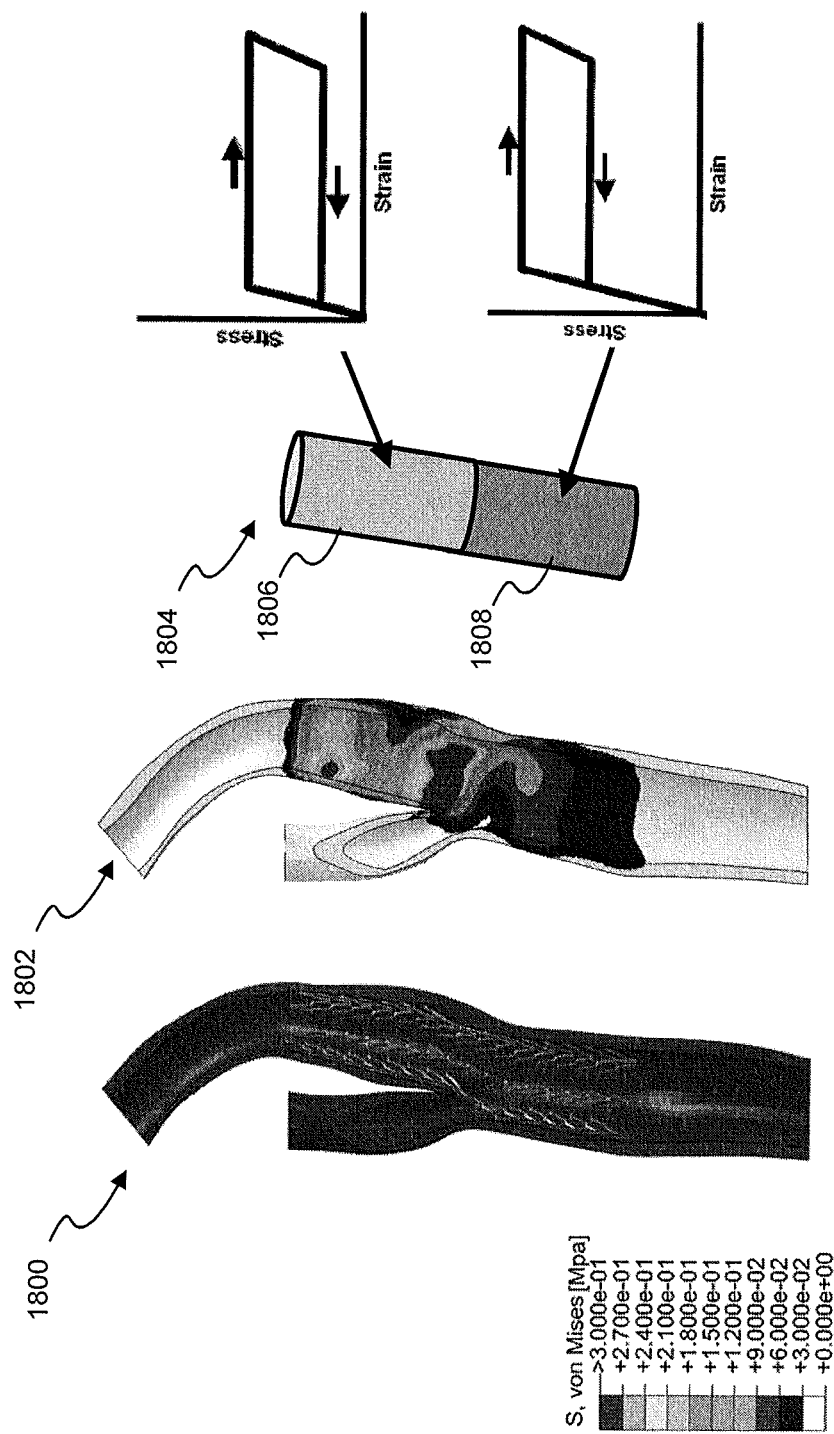
FIG. 14A illustrates an artery with differing diameter and its force profile.
FIG. 14B illustrates a side view of a stent using MMM.

Systems, apparatuses and methods described herein can also be useful in the field of medical stents. FIG. 14A illustrates an artery with differing diameters along its length (the author of the illustration being F. Aurichio). Due to the differing diameter, an artery may provide different pressures onto a stent inserted into the artery. An example force profile of an artery 1802 is illustrated in FIG. 14A. As shown in FIG. 14B, a stent fabricated from MMM 1804 may be configured to have regions of differing pseudo-elasticity; in this example, a region of greater elasticity 1806 and a region of less elasticity 1808. As such, the portions of the stent destined for smaller diameter arteries may be configured to have more elasticity than portions of the stent destined for greater diameter arteries. Having the pseudo-elasticity of the stent 1804 differ depending on the diameter of the artery may provide for easier installation by a physician and avoid potential tissue damage and stent damage.

Figure 15:
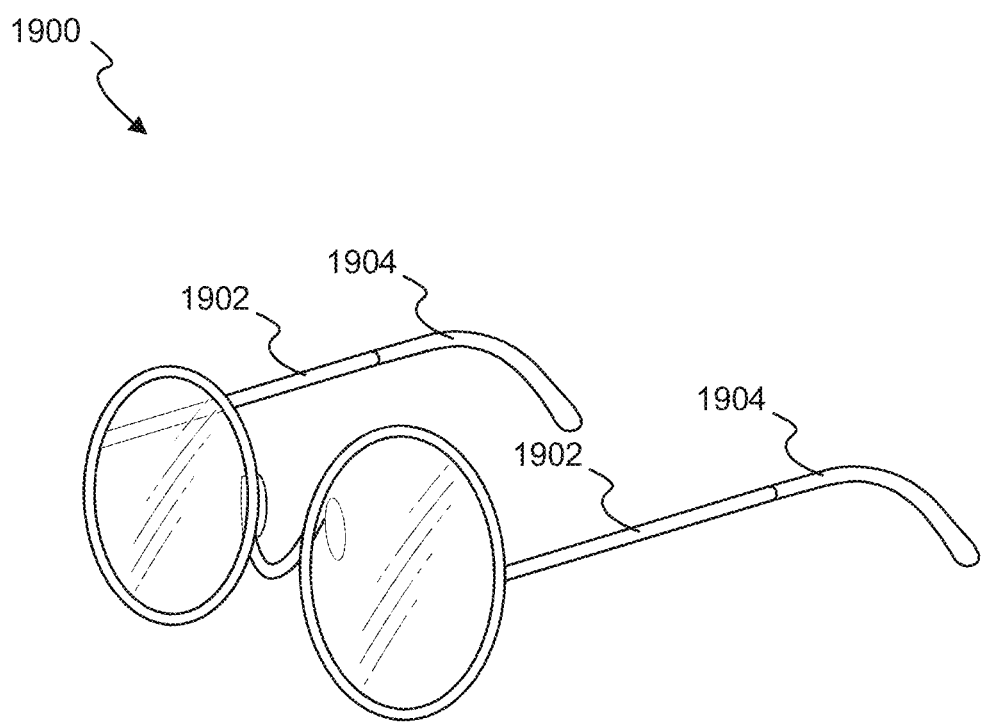
FIG. 15 illustrates a perspective view of eyeglasses using MMM.

Systems, apparatuses and methods described herein can also be useful in the field of eyeglasses. FIG. 15 illustrates a perspective view of eyeglasses 1900 using MMM. The eyeglasses 1900 include a frame having two arms. A first portion of the arms 1902, located at the proximate end of the arms, may be composed of unprocessed shape memory material such that the first portion 1092 does not have a transformation temperature. A second portion 1904, located at the lateral end of the arms, may be processed, using the processes described herein, to have a shape memory. In an example, when the second portion 1904 is at room temperature, the second portion 1904 is substantially in-line with the first portion 1902. When the second portion 1904 is substantially in-line with the first portion 1902, the eyeglasses 1900 may be placed on a user's head with greater ease as, in contrast with conventional eyeglasses that have a rounded profile at the end of the frame arms, the eyeglasses 1900 do not have to be maneuvered around the user's ear. After the eyeglasses 1900 are placed on the user's head, the body heat of the user will raise the temperature of the second portion 1904. When the temperature of the second portion 1904 reaches the transformation temperature, the second portion 1904 takes on a curved profile similar to that of conventional eyeglasses. As maneuvering around the user's ear is avoided, the curve of the second portion 1904 can be configured to snuggly seat around the user's ear, providing a secure fit. Additionally, the pseudo-elastic flexibility of the MMM can enhance the eyeglasses 1900 resistance to breakage or fracture.

Figure 16:
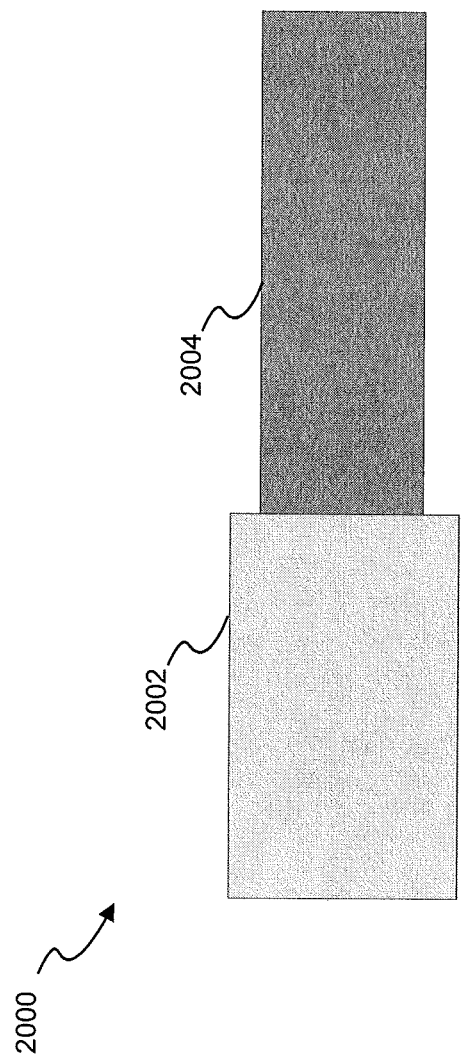
FIG. 16 illustrates a side view of a linear actuator using MMM.

Systems, apparatuses and methods described herein can also be useful for actuators. FIG. 16 illustrates a side view of a linear actuator 2000 using MMM. The linear actuator 2000 includes a static portion 2002 and an actuating portion 2004. The static portion 2002 may be composed of unprocessed shape memory material such that the static portion 2002 does not have a transformation temperature. The actuating portion 2004, located at the lateral end of the static portion 2002, may be processed, using the processes described herein, to have a shape memory. In an example, at a first temperature, the length of the actuating portion 2004 is more condensed along the longitudinal axis. When a second temperature is applied, the length of the actuating portion 2004 increases due to the shape memory material reaching the transformation temperature. In some cases, the actuating portion 2004 may be processed to have multiple transformation temperatures such that the actuating portion 2004 may be configured to reach different lengths relative to the static portion 2002.

In further cases, the static portion 2002 may be processed to have a transformation temperature. In these cases, the actuating portion 2004 may be situated in a cavity in the static portion 2002. When the second temperature is applied, the static portion 2002 changes shape which pushes the actuating portion 2004 at least partially out of the cavity in the static portion 2002 and causes the actuating portion 2004 to actuate linearly. In other cases, the same principles of MMMs may be used to fabricate other types of actuators, for example, rotary actuators, valve actuators, or the like. An actuator using MMM may provide ease of manufacturing, reduced costs and reduced maintenance as there are fewer moving parts than a traditional actuator. An MMM actuator may itself be used in various applications; for example, as a temperature activated opening for a beverage container.

In some cases, the linear actuator 2000 may function like an electrically activated actuator. The linear actuator 2000 may be connected to an electrical circuit. When a current is passed from the circuit into the linear actuator 2000, resistive heating may occur in at least a portion of the linear actuator 2000. The resistive heating may cause the components of the linear actuator 2000 to reach the transformation temperature, and thus, actuate the linear actuator 2000. It is intended that having an electrical activated actuator may lower costs and reduce maintenance requirements when compared to an actuator that is motorized, pneumatic, or the like. Electrical resistive heating may be used for any application of MMMs in order to have the MMM reach a transformation temperature; further example applications may include electrically activated switches, valves, or the like.

Figure 17:
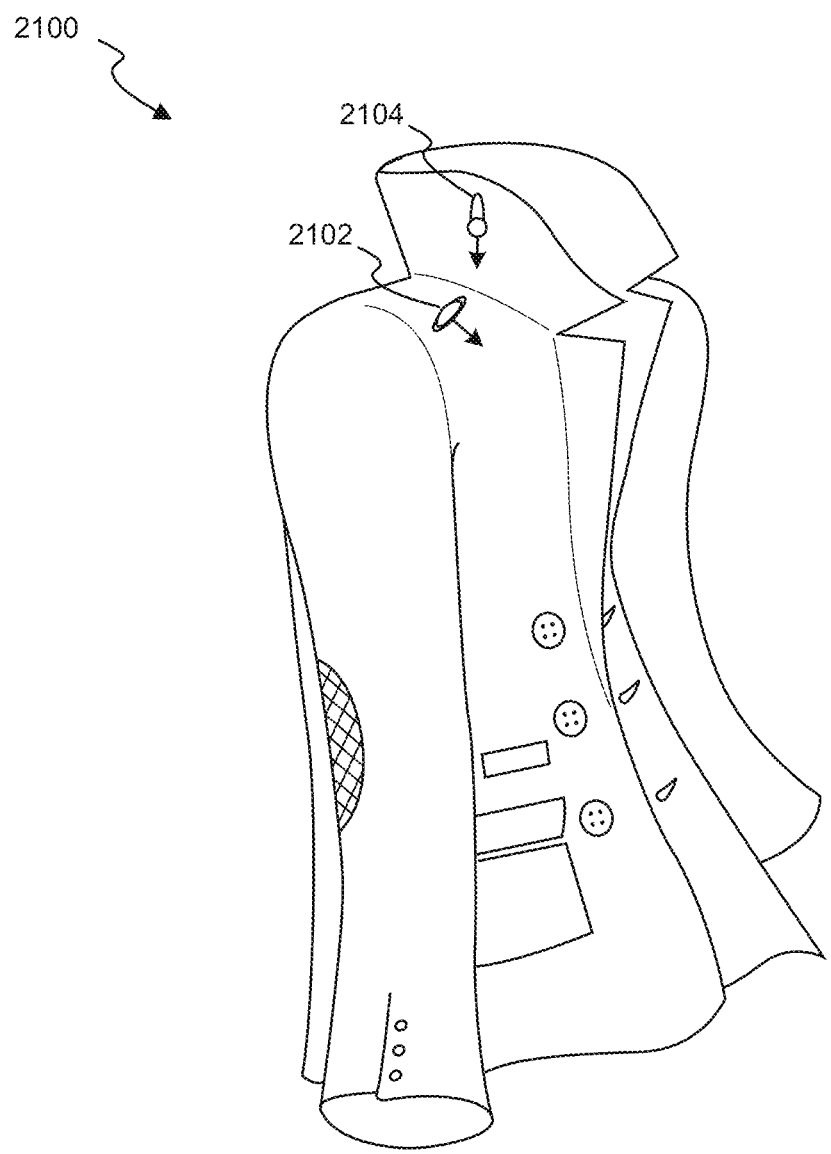
FIG. 17 illustrates a perspective view of a textile using MMM.

Systems, apparatuses and methods described herein can also be useful in the field of textiles. FIG. 17 illustrates a perspective view of a textile 2100, in this case a coat, using MMM. The textile 2100 includes a first flap 2102 and a second flap 2104. The material of the textile 2100 covering the flaps 2102, 2104 may be processed, using the processes described herein, to have various transformation temperatures. During "normal" temperatures, the flaps 2102, 2104 may be configured to cover the respective holes in the textile 2100. As the temperature changes, the flaps 2102, 2104 may be configured to uncover the respective holes in the textile 2100. In some cases, the first flap 2102 may have different transformation temperatures than the second flap 2104. In this way, when a user is wearing the textile 2100 and the user's body temperature, and/or the ambient temperature, reaches a predetermined threshold, the flaps 2102, 2104 automatically open allowing cooling of the user. In some cases, the flaps 2102, 2104 may be connected to an electric circuit such that when current is passed into the flaps 2102, 2104, either automatically or by choice of the user, the flaps 2102, 2104 resistively heat and reach the transformation temperature.

Figure 18:
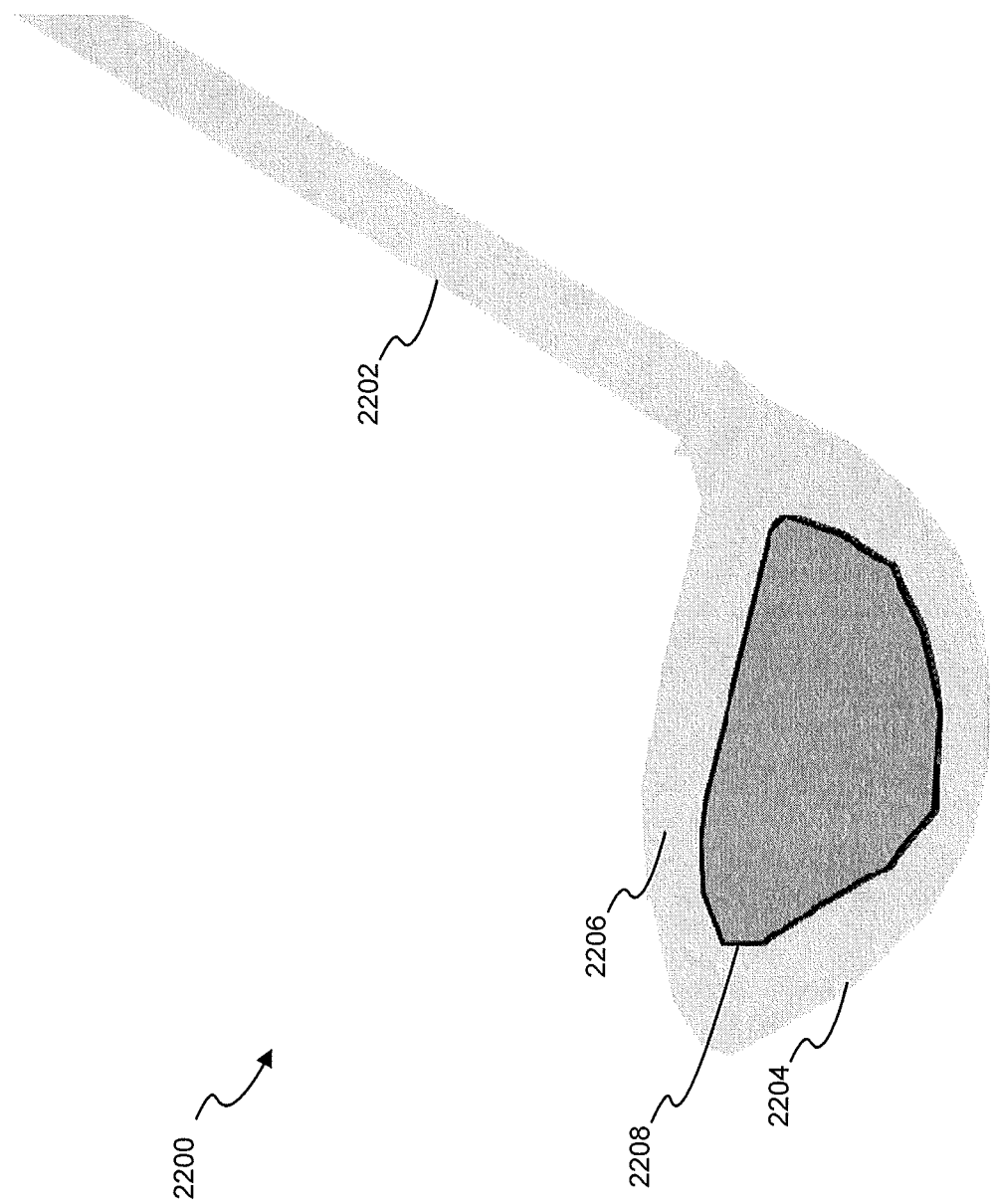
FIG. 18 illustrates a side view of a golf club using MMM.

Systems, apparatuses and methods described herein can also be useful in the field of sports equipment. FIG. 18 illustrates a side view of a golf club 2200 using MMM. The golf club 2200 includes a shaft 2202 and a head 2204. The head 2204 includes a body 2206 and a face 2208 that is mounted at the front of the body 2206. In further cases, the face 2208 may be integral to the body 2206. In this example, the face 2208 is composed of a planar sheet of MMM or of strips of MMM affixed together. The face 2208 may be configured such that different areas of the face 2208 have different pseudo-elastic properties. Configuring different areas of the face 2208 to have different pseudoeleastic properties can allow the golf equipment manufacturer to alter the characteristics of different areas of the face 2208; for example, different areas of the face 2208 may have different ball absorption times, different elastic properties, different hardness, or the like. It is intended that configuring different areas of the face 2208 to have different pseudo-eleastic properties may permit certain playing advantages; for example, allowing greater projectile distance when the center of the face 2208 is struck without having the rest of the face 2208 be overly malleable.

The aforementioned applications and uses of the systems and methods described herein and of MMMs produced using this processing generally are only a sampling of the type of applications envisioned.

In the preceding description, for purposes of explanation, numerous details are set forth in order to provide a thorough understanding of the embodiments. However, it will be apparent to one skilled in the art that these specific details may not be required. In other instances, well-known electrical structures and circuits are shown in block diagram form in order not to obscure the understanding. For example, specific details are not provided as to whether aspects of the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

We claim:

1. An apparatus for fabrication of a multiple memory material comprising:
   a feeding assembly for feeding shape memory material;
   a processing station aligned with the feeding assembly to receive the shape memory material to be processed, the processing station comprising:
      a material passageway passing though the processing station and aligned with the feeding assembly to receive and retain the shape memory material from the feeding assembly; and
      at least one energy source aperture aligned with the material passageway;
   a shielding gas engagement portion to provide shielding gas to the material passageway;
   at least one energy source aligned with the energy source aperture to provide energy to the shape memory material;
   a shielding gas provider attached to the shielding gas engagement portion to provide shielding gas; and
   a controller configured to control the feeding assembly, the shielding gas provider and the energy source according to predetermined parameters to form the multiple memory material;
   wherein the material passageway is configured to generally match a size of the shape memory material while still allowing movement of the shape memory material through the material passageway.

2. The apparatus in claim 1, wherein the shielding gas engagement portion is located on a lateral side of the processing station and the at least one energy source aperture is located on a top portion of the processing station.

3. The apparatus of claim 1 wherein the processing station further comprises a first and a second roller assembly for retaining the material.

4. The apparatus of claim 1, wherein the feeding assembly comprises an upper roller assembly and a lower roller assembly wherein one of the roller assemblies is driven by a motor and the other roller assembly is free spinning.

5. The apparatus of claim 1, wherein the feeding assembly is a robotic arm.

6. The apparatus of claim 1, wherein the feeding assembly feeds the material to the processing station in a continuous feed.

7. The apparatus of claim 1, wherein the feeding assembly feeds the material to the processing station in a stepped manner.

8. The apparatus of claim 1 further comprising a guidance assembly proximate to the processing station configured to guide the multiple memory material after exiting the processing station.

9. The apparatus of claim 1 wherein the shape memory material is a wire.

10. The apparatus of claim 1, wherein the shape memory material is a sheet.

11. A method for fabricating a multiple memory material comprising:
    determining process parameters for the multiple memory material, via a controller;
    receiving shape memory material at a feeding assembly;
    feeding the shape memory material, via the feed assembly, to a processing station,
    the processing station including a material passageway passing though the processing station and aligned with the feeding assembly to receive and retain the shape memory material from the feeding assembly wherein the material passageway is configured to generally match a size of the shape memory material while still allowing movement of the shape memory material through the material passageway;
    providing shielding gas to the processing station, via a shielding gas provider; and
    providing energy to the shape memory material, via at least one energy source, based on the process parameters to produce the multiple memory material.

12. The method of claim 11 further comprising:
    determining if there are additional areas of the shape memory material to process; and
    feeding the shape memory material through the processing station to the additional area for processing.

13. The method of claim 11, wherein the multiple memory material is a wire.

14. The method of claim 11, wherein the multiple memory material is a sheet.

15. A medical stent comprising a region of greater elasticity and a region of lesser elasticity, wherein the stent is fabricated according to the method of claim 11.

16. A pair of eyeglasses comprising:
    a frame;
    two multiple memory arms extending from the frame, wherein each arm comprises:
       a first portion at a proximate end of the arm composed of unprocessed shape memory material; and
       a second portion at a lateral end of the arm composed of shape memory material, processed according the method of claim 11, wherein the second portion is substantially in-line with the first portion at a first temperature and wherein the second portion is adapted to change profile when heated to a second temperature.

17. A textile comprising a multiple memory material processed according to the method of claim 11, wherein the material is covered by the textile and is configured to adjust the shape of the textile based on changes in temperature.

18. A golf club head comprising:
    a body; and
    a face mounted to the front of the body, wherein the face comprises a multiple memory material processed according to the method of claim 11 to have different pseudo-elastic properties in different areas of the face.

19. An endodontic file comprising:
    a handle; and
    a filing wand connected to the handle, the filing wand comprising a multiple memory wire processed according to the method of claim 11 to have multiple pseudo-elastic properties to adapt to the shape of a root canal.

20. An orthodontic archwire comprising a plurality of force regions having differing tensile force, wherein the archwire is fabricated according to the method of claim 11.

* * * * *